United States Patent [19]
Gronbech-Jensen et al.

[11] Patent Number: 5,553,004
[45] Date of Patent: Sep. 3, 1996

[54] CONSTRAINED LANGEVIN DYNAMICS METHOD FOR SIMULATING MOLECULAR CONFORMATIONS

[75] Inventors: Niels Gronbech-Jensen, Santa Fe, N.M.; Sebastian Doniach, Menlo Park, Calif.

[73] Assignee: The Board of Trustees of the Leland Stanford Jr. University, Palo Alto, Calif.

[21] Appl. No.: 151,278

[22] Filed: Nov. 12, 1993

[51] Int. Cl.$^6$ .................................................. G06F 17/50
[52] U.S. Cl. ................................. 364/496; 364/578
[58] Field of Search ......................... 364/578, 496–499, 364/524, 527; 436/15

[56] References Cited

U.S. PATENT DOCUMENTS

| | | | |
|---|---|---|---|
| 4,704,692 | 11/1987 | Ladner | 364/496 |
| 4,853,871 | 8/1989 | Pantoliano et al. | 364/496 |
| 5,025,388 | 6/1991 | Cramer, III et al. | 364/496 |
| 5,241,470 | 8/1993 | Lee et al. | 364/496 |
| 5,265,030 | 11/1993 | Skolnick et al. | 364/496 |
| 5,386,507 | 1/1995 | Teig et al. | 395/161 |

OTHER PUBLICATIONS

Karplus, Martin and Weaver, David L., "Protein–folding dynamics", Apr. 1, 1976, Nature, vol. 260. pp. 404–406.

Gunateren, Van, W. F. and Berendsen, H. J. C., "A leap–Frog Algorithm for Stochastic Dynamics", 1988, Molecular Simulation, vol. 1.

Bhattacharya, D. K., Clementi, E., and Xue, W., "Stochastic Dynamic Simulation of a Protein", International Journel of Quantum Chemistry, Jun. 5, 1992, vol. 42, pp. 1397–1408.

Nadler, Walter, Brunger, Axel T., Schulten, Klaus, and Karplus, Martin, "Molecular and stochastic dynamics of proteins", 1987, Proc. Natl. Acad. Sci. U.S.A., vol. 84 pp. 7933–7937.

Lamm, Gene and Szabo, Attila, "Langevin modes of macromolecules", Dec. 15, 1986, J. Chem. Phys. 85 vol. 12, pp. 7344–7348.

Widmalm, Jordan and Pastor, Richard W., "Comparison of Langevin and Molecular Dynamics Simulations", 1992, J. Chem. Soc. Faraday Trans. 88 vol. 13, pp. 1747–1754.

Deutsch, J. M. and Madden, T. L., "Theoretical studies of DNA during gel electrophoresis", 1989, Journal of Chemical Physics, vol. 90, pp. 2476–2485.

Jorgensen, William L. and Tirado–Rives, Julian, "The OPLS Potential Functions for Proteins. Energy Minimizations for Crystals of Cyclic Peptides and Crambin", 1988, American Chemical Society. vol. 110, pp. 1657–1666.

Gunsteren, Van, W. F., "Algorithms for macromolecular dynamics and constraint dynamics", 1977, Molecular Physics, vol. 34, pp. 1311–1327.

(List continued on next page.)

*Primary Examiner*—Emanuel T. Voeltz
*Assistant Examiner*—Kyle J. Choi
*Attorney, Agent, or Firm*—Hickman Beyer & Weaver

[57] ABSTRACT

The present invention provides a constrained stochastic dynamical method for simulating the motion of a molecular system. The method simulates the motions of atoms within the molecular system by evaluating first order force expressions for all the atoms over a series of time steps. The force expressions include terms for frictional forces, non-covalently interatomic forces, thermal noise forces, and covalent constraining forces. Relatively long time steps can be used because the fast motions (such as vibrations associated with covalent bonds) are not explicitly considered. Rather, the fast molecular motions associated with covalent bonds are averaged around their equilibrium bond lengths and, in some cases, bond angles. This is implemented by introducing (1) thermal noise forces, and (2) constraining forces fixing the relative positions of some atoms based upon their covalent bonds. Because the method treats the movement of atoms within a molecular system as overdamped, the atomic force balances are first order force expressions which can be evaluated without iteration.

44 Claims, 22 Drawing Sheets

OTHER PUBLICATIONS

Kitao, Akio, Hirata, Fumio, and Go, Nobuhiro, "The effects of solvent on the confirmation and the collective motions of protein: normal mode analysis and molecular dynamics simulation of melittin in water and in vacuum", 1991, Chemical Physics, 158, pp. 447–472.

Kottalam, J. and Case, D. A., "Langevin Modes of Macromolecules: Applications to Crambin and DNA Hexamers", 1990, Biopolymers, vol. 29, pp. 1409–1421.

Jean–Charles, et al., "Electrostatic contributions to solvation energies: comparision of . . .", 1991, Journal of the American Chemical Society, (abstract), vol. 113, pp. 1454–1455.

Sharp, K. A., et al., "Calculating total Electrostatic energies with . . .", 1990, Journal of Physical Chemistry, (abstract), vol. 94, pp. 7684–7692.

Tuckerman et al., "Stochastic molecular dynamics in systems with multiple time scales and memory friction," *Journal of Chemical Physics,* vol. 95, No. 6, Sep. 1991, pp. 4389–4396. (Abstract only).

Sese et al., "On the description of atomic motions in dense fluids by the gernalized Langevin equation: statistical properties of random forces," *Journal of Statistical Physics,* vol. 60, No. 3–4, Aug. 1990, pp. 501–518 (Abstract only).

CONSTRAINED LANGEVIN DYNAMICS METHOD FOR SIMULATING MOLECULAR CONFORMATIONS

BACKGROUND OF THE INVENTION

This invention relates to methods for determining the relatively long time dynamics of molecular systems. The method also predicts the conformations of macromolecular systems including those that have undergone mutation.

Predicting how molecules move and what conformations they adopt is a problem that has important consequences in a variety of commercially important technical areas. For example, new drug development increasingly relies on the rapid prediction of molecular conformations to identify a few promising candidate compounds. By identifying from a large pool of candidate compounds those few possessing conformations consistent with a desired activity, the researcher saves considerable time that would be lost synthesizing and testing many different compounds.

One widely-used procedure for simulating the motions and conformations of molecules, and especially proteins, is molecular dynamics. Molecular dynamics computations are now extensively used for refining molecular structures obtained by X-ray or NMR techniques and for calculating the free-energy differences essential to correct evaluation of binding equilibria and the changes introduced by site-specific mutagenesis. Generally, in a molecular dynamics simulation, one expresses all the forces tending to change the positions of atoms within the molecule and then integrates Newton's force equation (F=ma) to obtain velocities and positions of the atoms in the molecule at a specified temperature. The relevant forces employed in a molecular dynamics simulation include both interatomic covalent and non-covalent forces. By repeatedly moving the atoms to new locations and then integrating over an appropriately short length of time (the "time step"), researchers can predict the motions of atoms within a molecule over a relatively short time frame.

The dynamics of a macromolecule comprises an enormous range of time scales including atomic vibrations on a subpicosecond time scale, amino acid rotational isomerization on a nanosecond time scale, and nucleation for helix formation on a 100 ns time scale. Molecular dynamics often provides a quite accurate description of the faster events (e.g. vibrations on a covalent bond) but can not be extended to the very much longer time scales where many events of commercial importance occur. This is because the accuracy of molecular dynamics simulation relies on careful numerical treatment at the level of the fastest time scale in the problem, thus requiring too much computational effort to reach the longer time regimes. This especially true when solvent molecules are explicitly included in the model, as is sometimes necessary to accurate describe motion. The time steps employed in molecular dynamics simulations are typically of the order of a few femtoseconds. Thus, given current computational power, a few 10 s of picoseconds (up to possibly 1 nanosecond) is the longest realistic time frame for molecular simulation. Unfortunately, this falls far short of the time domain over which such interesting large scale events as protein folding, opening fluctuations, and helix-coil transitions take place. Even with advances in computer technology such as progress in parallel computing, molecular dynamics may still be unable to describe such large-scale motions of macromolecules.

In order to overcome these limitations, it becomes necessary to introduce simplifying assumptions about the forces and the motions they cause within molecular systems. If these assumptions are formulated approximately correct, a sufficiently accurate simulation can be preserved while the simulation is extended into much longer time domains. One widely used assumption is that some of the fast modes of the molecule can be locally averaged and described as random noise forces that are balanced by frictional forces. This approach is gaining popularity and is especially important in simulations accounting for the effect of solvent on the molecular motions (i.e., Brownian motion). Because the noise forces introduce a statistical component, these simulations have been referred to as "stochastic dynamics." They are also often referred to as "Langevin dynamics" because the relevant force expressions containing frictional and noise forces are known as Langevin equations of motion.

Unfortunately, most stochastic dynamics methods still explicitly consider all the intramolecular motions, fast and slow, considerably limiting applicability of the simulation to long time molecular events. For example, Bhattacharya et. at. in *International Journal of Quantum Chemistry*, 42:1397–1408 (1992) describe a stochastic dynamics model of a small protein (bovine trypsin inhibitor) in which covalent and non-covalent forces are explicitly considered. The simulation employs a Langevin dynamics expression including covalent constraining forces and relatively complex frictional terms to account for the effects of water molecules. The authors claim that their method is one order of magnitude faster than a comparable molecular dynamics method, but this is still too slow to observe many interesting events.

Because the covalent forces associated with molecular systems are responsible for the faster motions such as bond vibrations, it might be useful to remove them from explicit consideration in the simulation. A 1977 paper (van Gunsteren and Berendsen, *Mol. Phys.*, 34:1311–1327 (1977)) describes macromolecular dynamics method in which the covalent bond forces are replaced with constraint forces which simply maintain the relative positions of atoms bonded to one another within the molecular representation. In the molecular modeling community, a widely-used version of this procedure is known as "SHAKE." The method employs Newton's motion equations to model the motion resulting from the relevant forces. Like the other approaches to molecular and stochastic dynamics, these equations are second order (i.e. they include terms having second derivatives with respect to time). Thus, the method must determine not only the force acting on each atom but also the change in velocity. Such equations must then be solved by iteration (and therefore many matrix inversions) at each time step. This considerably complicates and slows the process.

Recently, Deutch et al. (*Journal of Chemical Physics*, 90:2476–2485 (1989)) described a stochastic technique for modeling the movement of DNA during gel electrophoresis. The authors modeled the DNA as a thread with beads and the gel as an infinite lattice of obstacles through which the thread and beads moved. They used a Langevin force description including terms for friction between the bead and a solvent, a constraining force between adjacent beads, a force between the beads and the obstacles, a random force acting on the beads, and a force of an applied electric field. This work is interesting in that it employs constraining forces in the Langevin description of molecular motion and employs first order equations which can be solved rapidly. However, it treats the DNA molecule as an extended chain of beads which do not interact with one another, other than through the constraining forces. In other words, it fails to account for the non-bonding interatomic potentials between the atoms comprising the DNA molecule. While this may be an adequate assumption for some macromolecular movements, for many other systems such as proteins and peptides, molecular movements and conformations are largely determined by non-bonding interatomic forces. Thus, the approach of Deutch et al. is inadequate for describing the dynamics of many important macromolecular systems.

Although conventional molecular dynamics and stochastic dynamics methods are useful in describing molecular events occurring on fast time scales, it would be desirable to have accurate methods of describing events on slower time scales.

SUMMARY OF THE INVENTION

The present invention provides a constrained stochastic dynamical method for simulating the long time motion of a molecular system. The method simulates the motions of atoms within the molecular system by evaluating overdamped force balances for all the atoms over a series of time steps. The force expressions include terms for frictional forces, non-covalent interatomic forces, thermal noise forces, and covalent constraining forces. Relatively long time steps can be used because the fast motions (such as vibrations associated with covalent bonds) are not explicitly considered. Rather, the fast molecular motions associated with covalent bonds are averaged around their equilibrium bond lengths and, in some cases, bond angles. This is implemented by introducing (1) the thermal noise forces, and (2) the constraining forces fixing the relative positions of some atoms based upon the geometry of their covalent bonds. Because the invention employs constraining forces in place of covalent forces, the faster events such as bond vibrations need not be explicitly considered. Further, because the method treats the long time movement of atoms within a molecular system as overdamped, the atomic force balances are first order force expressions which can be evaluated by a simple matrix inversion without iteration. The combination of these advances considerably speed the simulation process.

In the methods of this invention, a representation of a molecular system is initially prepared in a computer usable form. The representation includes atoms held in relationship to one another by chemical bonds. Although the chemical bonds do constrain the available arrangements of atoms with respect to one another, they do not completely determine the molecular structure. There will still be some degrees of freedom, such as rotation about some single bonds, which allow the molecular system some latitude in its conformations. The particular conformation adopted within the range of freedom afforded by these degrees of freedom can be set based upon known structures such as homologs of the molecular system being modeled. Alternatively, the starting conformation can be set in a completely random conformation—within the constraints imposed by the chemical bonds.

After the molecular representation has been preprocessed (i.e. put in a computer usable form), a set of covalent constraining forces are defined for each atom. Preferably, these include forces constraining two atoms covalently bonded to one another to remain a fixed distance apart, with the distance being defined by the equilibrium covalent bond length. In addition, two atoms not covalently bonded to one another may be constrained in their relative positions by a fixed covalent bond angle. Beyond the relationships fixed by these constraining forces, the atoms are free to move with respect to one another as permitted by the degrees of freedom.

Next, various forces acting on each atom of the representation are determined. These include the interatomic non-covalent forces experienced by each atom as a result of its position with respect to neighboring atoms. Preferably, the non-covalent forces account for at least electrostatic and van der Waals potentials caused by interactions between the atom under consideration and other atoms within defined cut off distance. In addition to the non-covalent interatomic forces, a thermal noise term accounting for the bond vibrations and other rapid molecular motions is included. The thermal noise force is preferably generated by a random number generator following a gaussian distribution. In order to model the fact that these forces (from non-bonding interatomic potentials and noise) are only able to move the atoms in directions within the allowed degrees of freedom (i.e., they are unable to move the atoms in directions constrained by covalent bonds and bond angles), components of the interatomic potential in the directions of the constraining forces are projected out. In other words, the force components in the direction of the constraining forces are removed from the non-bonding and noise forces by vector subtraction. In addition to the non-covalent, thermal noise, and constraining forces, the atomic motions are influenced by frictional forces. Thus in the force balances of this invention, the forces tending to move the atoms are non-covalent interatomic forces and noise forces, while the forces tending to limit motion are covalent constraining forces and frictional forces.

The above forces are incorporated in an overdamped Langevin dynamics force balance for each atom. These expressions are then evaluated over a defined length of time (a time step) to identify a new conformation of the molecular representation. In essence, the new conformation is a result of molecular motion brought about by the forces acting on the atoms of the molecular system. Because there may be many atoms in the molecular system, it is often convenient to evaluate the Langevin dynamics expression in matrix and vector form, with each row of the matrix describing the forces acting on a single atom. In a preferred embodiment, the time step is between about 0.5 and 10 picoseconds. For many molecular systems, the atoms may move by approximately one-thousandth of an Å over this time, a distance representing average motion. Although comparable distances are typically obtained with the much shorter time steps of molecular dynamics simulations, these represent oscillatory motion of covalent bonds, much of which averages out over time. After the new positions of the atoms have been identified at the end of the time step, the atoms of the molecular representation are moved to these locations and a new set of forces are determined (at least the non-bonding interatomic and thermal noise forces). Typically, the process will march through multiple such time steps until it provides the desired conformational and/or dynamical information about the molecule. Typically, after a number of time steps, the molecular representation will evolve to low energy conformations reflecting the actual conformations of the molecular system. This is especially valuable if the real conformation of the molecular system under consideration (or a related molecular system) is unknown.

In a preferred embodiment, the molecular system being investigated is a peptide or protein and the degrees of freedom are the $\phi$ and $\Psi$ bond angles of an amino acid, and, in some embodiments, certain $\chi$ bond angles associated with side chain rotations. In other preferred embodiments, another degree of freedom is the $\omega$ torsion angle between two adjacent amino acids in a peptide chain. All other bond angles are fixed as are all bond lengths. These values are fixed and used in the constraining forces.

In another aspect, the present invention provides a method of producing molecular systems having specified chemical properties such as binding affinity for a ligand. This is accomplished by first identifying a group of compounds potentially having the desired property. Initial molecular representations for each of the potential compounds are prepared in a computer usable form. Thereafter overdamped Langevin force balances are prepared for each atom in each compound as described above. The conformations of each compound in the group are allowed to evolve by marching through multiple time steps until the compounds can be evaluated for the desired property. This may involve for example, determining whether a ligand can be bound in a binding site of the compounds being simulated. One or more compounds shown by the simulation to have the desired properties are thereafter prepared by, for example, chemical synthesis or recombinant expression and their properties subsequently tested.

These and other features of the present invention will be presented in more detail in the following specification of the invention and the figures.

DESCRIPTION OF THE PREFERRED EMBODIMENTS

I. Definitions

Figure 1:
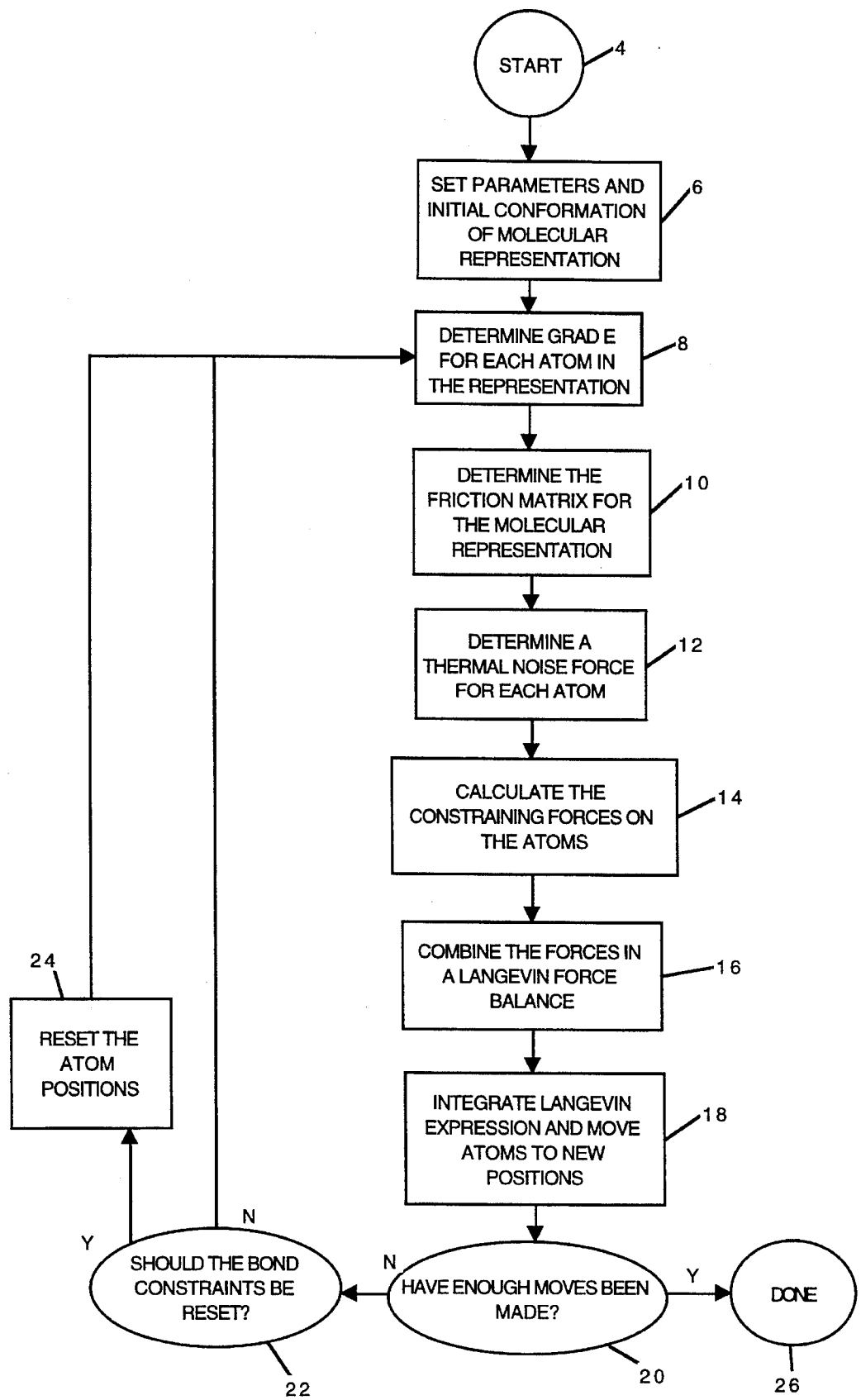
FIG. 1 is a process flow chart showing an overview of the process steps employed in a preferred embodiment of this invention.

"Molecular system" refers to a collection of atoms, all of which are covalently bonded to some other of the atoms. In addition to the covalent bonds, the atoms interact with one another via a defined set of noncovalent interactions. These may include van der Waals forces, hydrogen bonding, electrostatic forces, hydrophobic interactions, etc. A molecular system may be a species in any chemical class such as organic compounds (macromolecules and smaller molecules) and inorganic compounds including water. Further, it may exist in a gas, liquid, or solid phases, or an equilibrium mixture of the two or three phases.

The "degrees of freedom" associated with molecular systems are adjustable parameters which when set to specific values define the conformation of a molecular system. Examples of degrees of freedom associated with molecular systems include rotation, bending about the vertex of a bond angle, vibration, etc. A degree of freedom may also be used to describe independent ways that a molecular system may take up energy.

"Macromolecule" generally refers to a large molecule, sub-molecular group, or complexes between one or more molecules or groups. A macromolecule will generally have a molecular weight of more than about 200, preferably more than about 500, and most preferably more than about 1000 (one kilodalton). For comparison, a typical small protein is 15–20 kilodaltons. A macromolecule will typically have a main-chain or "backbone" which is a string of repeating molecular units. In addition, the macromolecule may possess a series of side-chains extending from the main-chain. Examples of macromolecules include, proteins and large peptides alone or associated with other molecules such as cofactors, substrates, membranes, and cell structural organelles. Macromolecules may also include nucleic acids such as DNA and RNA, as well as these materials combined with materials such as histones, ribosomes, and polymerases.

"Mutant" refers to any molecular system that has been modified to deviate from its native state. In the context of protein or peptide structures, a mutant is expressed by a mutation (i.e. an alteration in the amount or arrangement of genetic material of a cell or virus) such that one or more amino acids in the peptide have been deleted or changed. In most instances, the mutant will retain most of the structural information of the parent wild type structure (i.e. the common form of a biological molecule occurring in nature). A mutant may also be a peptide containing one or more amino acids that are not genetically coded in naturally occurring proteins.

A "representation" refers to a geometric model of a real molecular system. The representation will have an arrangement of structural features and degrees of freedom that correspond to those of the real molecular system. Through manipulations on a computer or other means for rapidly evaluating force expressions, the representation may be evolved through a range of movements to explore the properties of a real molecular system in various conformations.

The following discussion of the preferred embodiment is framed in the context of a method for predicting peptide movements through one or more conformations. However, it should be understood that the principles discussed in the context of peptide conformations are general and will be equally applicable in the context of other macromolecular systems such as manmade polymers having defined degrees of freedom such as liquid crystals, and biological molecules such as nucleic acids, lipids, lipid bilayers, and polysaccharides. In addition, the discussion is primarily limited to certain degrees of freedom possessed by peptide main-chains and side-chains. However, there is no reason why the method of this invention could not be employed to predict other degrees of freedom within a peptide such as limited bending at certain bond angles.

II. Overview of the invention

At least two types of useful information can be obtained from the present invention: (1) the motions of the molecular components (atoms and molecular groups) with respect to one another, and (2) the average and permissible conformations of the atoms within the molecular system. Regarding the motions of molecular components, the dynamic fluctuation of protein components about their average conformations plays an important role in many biological processes such as enzyme activity, macromolecular recognition, and complex formations. Thus, an accurate description of protein motion can provide valuable incites into these processes and lead to medical and commercial advances.

With regard to the invention's ability to predict molecular conformations, the invention can be used to determine the three dimensional conformation of a complex molecule. This is a particularly useful feature when the molecule has not yet been synthesized, but is related to other complex molecules for which the structure/conformation is known. For example, the molecular system under consideration might be a modified receptor protein in which a short amino acid loop is inserted near the binding site of the known receptor protein. The researcher can use the tools of this invention to determine first whether the replacement sequence can ever be made to fit in the existing protein structure and second how the protein shape could change as a result of the replacement. If the substitution could not be made to fit in the desired location under any circumstances (because of bond lengths and rotation constraints), the researcher knows that it would be futile to attempt to synthesize a protein with the replacement structure.

If it can be shown that the insertion is physically possible, the methods of this invention can show how the protein might change shape to accommodate the ligand. Initially, they could show whether a ligand can possibly fit in the binding site. If the chemical bonds of the protein are in positions that prevent the ligand from ever entering the binding site, then a researcher would understand from this invention that synthesis and further study of the modified protein is not warranted. On the other hand, if this invention shows that the protein binding site is rendered more accessible and/or more specific by virtue of the insertion, the researcher might prepare and study the protein which previously existed only as a molecular representation in the simulation of this invention. The substituted protein could be a useful drug or other medical product. Other replacements might improve the thermal stability of a molecule known to have a desired property such as detergent action.

The invention simulates the movement of real molecular systems by repeatedly moving the atoms of the system under the influence of at least four forces: frictional forces, interatomic non-covalent forces, thermal noise forces, and constraining forces. After each movement of the molecular system to a new conformation, the above forces are redetermined and the atoms are again moved, but this time under the influence of the new forces. FIG. 1 provides an overview of a preferred method of carrying out this process. The process begins at 4 and proceeds to a step 6 where a representation of the molecular system is prepared in a computer usable format. This involves specifying the coordinates of the atoms within the representation (usually, but not necessarily, all the atoms in the molecular system being modeled), and setting initial parameters for each atom in representation. The details of this process are provided in connection with the discussion of FIG. 5 below. After step 6, the interatomic force acting on each atom of the representation is calculated in a step 8 by any of a number of techniques as discussed below. In a preferred embodiment, expressions for the interatomic potential energies between the atom under consideration and the other atoms in representation are first provided as a function of distance. These expressions are then differentiated with respect to the distance vectors between the atom under consideration and the other atoms in the representation to give forces. The force vectors are then summed to give the gradient of energy for each atom of the representation. After step 8, frictional force terms for the atoms are determined at a step 10 and thereafter thermal noise terms for the atoms are prepared at a step 12. Both the frictional and noise terms may be determined by a variety of techniques as will be described below. Typically, the frictional force is determined before the thermal noise force, but the interatomic noncovalent force need not be calculated before the frictional and noise forces. Thus, in some embodiments, step 8 could be determined after step 12.

At this point (after step 12), the interatomic non-bonding forces, the thermal noise forces, and the frictional forces have been described for each atom in the representation. Only the constraining forces remain to be calculated for each atom. These are determined in a step 14 of the FIG. 1. The constraining forces are meant to represent the constraining effect that covalent bonds and bond angles have on the atoms of the representation. Specifically, covalent bonds separate atoms by defined distances (bond lengths), and the appropriate constraining force maintains these distances between the atoms attached by the covalent bond. Similarly, two or more atoms bonded to the same third atom are related by a defined a bond angle, and an appropriate constraining force maintains this bond angle. The constraining forces employed in this invention are represented as vectors that exactly offset those components of the other forces (due to interatomic potential and noise) having the same direction as the covalent bonds or bond angle constraints. The frictional forces do not need to be offset because they will have a direction corresponding to that of the motion (i.e., orthogonal to the constraining forces). Each time a conformation of the molecular system is set, the directions of the constraint force vectors are known (i.e., the direction of the distance vectors between atoms fixed with respect to one another by the covalent bonds and bond angles). However, the magnitudes of the constraint forces remain unknown until the non-covalent and noise forces are determined. This is because the magnitude of the constraint necessary to exactly offset these other forces can be determined only after the magnitude and direction of the other forces are known. The methods associated with determining the constraining forces will be described in more detail below.

After the constraining forces are determined in a step 14, all the forces are combined in a series of Langevin force balances, one for each atom, in a step 16. A preferred Langevin force balance is given by the following expressions:

$$\Xi \dot{R} = -\nabla E + N + S \Rightarrow \dot{R} = \Xi^{-1}\{-\nabla E + NS\} \quad (1)$$

where $R=(r_1, r_2, \ldots, r_i, \ldots, r_p)^T$ is the position vector, $r_1=(x_i, y_i, x_i)^T$ is the Cartesian coordinate of the ith particle, $\Xi=(\xi_{ij})$ is the friction matrix acting on the individual atoms of the peptide, and $N=(\eta_1, \eta_2, \ldots, \eta_i, \ldots \eta_p)^T$ is the Langevin thermal noise where $\eta_i$ is the three dimensional noise force acting on the ith particle in the system. $\Xi$ will in general include hydrodynamic effects which will produce frictional correlations between different atoms. In this case, the $\xi_{ij}$ are is 3×3 matrix reflecting the Cartesian coordinates of the atoms. In the simplest case, $\Xi$ is a diagonal matrix in which diagonal elements are given by a friction constant. The total potential energy of the system is given by E and the gradient is $$\nabla = (\nabla_1, \nabla_2, \ldots, \nabla_i, \ldots, \nabla_p)^T$$

$$\nabla_i = \left( \frac{\partial}{\partial x_i}, \frac{\partial}{\partial y_i}, \frac{\partial}{\partial z_i} \right)^T$$

The vector $$S = \left( \sum_j s_{1j}(r_{1j} - r_1), \sum_j s_{2j}(r_j - r_2), \ldots \right. \quad (2)$$

$$\left. \sum_j s_{ij}(r_j - r_i), \ldots, \sum_j s_{pj}(r_j - r_p) \right)^T$$

represents the constraint forces required to maintain the geometry of the system, i.e. to precisely project out all the components of $\nabla E$ which tend to change the constrained distances in the molecule. The scalars $s_{ij}$ are only defined for i, j representing two atoms constrained in their relative motion.

The meaning and implementation of this Langevin force balance will be described below, but it is worth noting now that the expression contains no second order acceleration terms. This results from the assumption that the motions of atoms in this representation are overdamped (i.e., the frictional forces are so much more important than the atomic accelerations that the accelerations can be ignored). The positions of the atoms appear only in velocity terms of first order expressions. This allows each time step to be evaluated without iteration, representing a significant computational advantage over prior methods.

After the Langevin force balances have been prepared, the new positions of the atoms are determined by numerically integrating the velocity expressions in a step 18. As discussed below, various numerical integration techniques are suitable for use with the present invention. In a preferred embodiment, a Runge Kutta integrator, and more preferably a second order Runge Kutta integrator, is used to evaluate the movement of the atoms over a defined time step. The movements of the atoms will be limited to only certain degrees of freedom because the constraining forces eliminate one or more of the potential degrees of freedom in the molecular representation. For example, the constraining forces may set the bond lengths and many of the bond angles, leaving the atoms free only to rotate about the axes of certain covalent bonds.

After the Langevin expressions have been integrated, a decision step 20 determines whether enough moves have been made to complete the simulation. This might involve simply determining whether a predefined number of steps have been taken (corresponding to a specified length of time). Alternatively, it might involve determining whether the molecular representation has evolved to a predetermined state (such as adopting a conformation that binds with a ligand). Assuming that decision step 20 determines that further steps need to be taken, another decision step 22 determines whether the bond constraints need to be reset. Usually, this simply involves checking whether the number of steps taken equals a multiple of a predetermined "reset" number. If so, the positions of the atoms in the molecular representation are reset in a step 24. This is accomplished by constraining the atoms of the conformation with respect to one another according to the covalent constraint conditions and the current values of the degrees of freedom in the representation. Steps 22 and 24 are sometimes necessary because the Langevin expressions are evaluated numerically causing some inherent error in the bond lengths and bond angles to propagate over many time steps.

Whether or not the atomic coordinates are reset, the process returns to step 8 and then proceeds through steps 10, 12, 14, 16, and 18 as described above. In this cycle, however, new values of the forces are provided for the new locations of the atoms. The process then continues through steps 20, 22, and when necessary 24. The loop through this series of steps continues (once for each time step), until decision step 20 determines that enough moves have been made. At this point, the process is concluded at 26.

The results of the simulation may be used for identify likely candidate molecular systems for synthesis and further study. Often, the simulation will provide enough information to allow a researcher to decide whether or not the molecular system under consideration could have a desired property. If the simulation suggests that the molecular system could be valuable, the actual compound may be prepared (and subsequently tested) according well-known methods such as peptide synthesis methods described below.

III. Processing Technique

The invention employs various process steps involving data stored in computer systems. These steps are those requiring physical manipulation of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bit patterns, values, elements, variables, characters, data structures, or the like. It should remembered, however, that all of these and similar terms are to be associated with the appropriate physical quantities and are merely convenient labels applied to these quantities.

Further, the manipulations performed are often referred to in terms, such as adding, running, or evaluating. In any of the operations described herein that form part of the present invention, these operations are machine operations. Useful machines for performing the operations of the present invention include general purpose digital computers or other similar devices. In all cases, there should be borne in mind the distinction between the method of operations in operating a computer and the method of computation itself. The present invention relates to method steps for operating a computer in processing electrical or other physical signals to generate other desired physical signals.

The present invention also relates to an apparatus for performing these operations. This apparatus may be specially constructed for the required purposes, or it may be a general purpose computer selectively activated or reconfigured by a computer program stored in the computer. The processes presented herein are not inherently related to any particular computer or other apparatus. In particular, various general purpose machines may be used with programs written in accordance with the teachings herein, or it may prove more convenient to construct a more specialized apparatus to perform the required method steps. The required structure for a variety of these machines will appear from the description given below.

Figure 2:
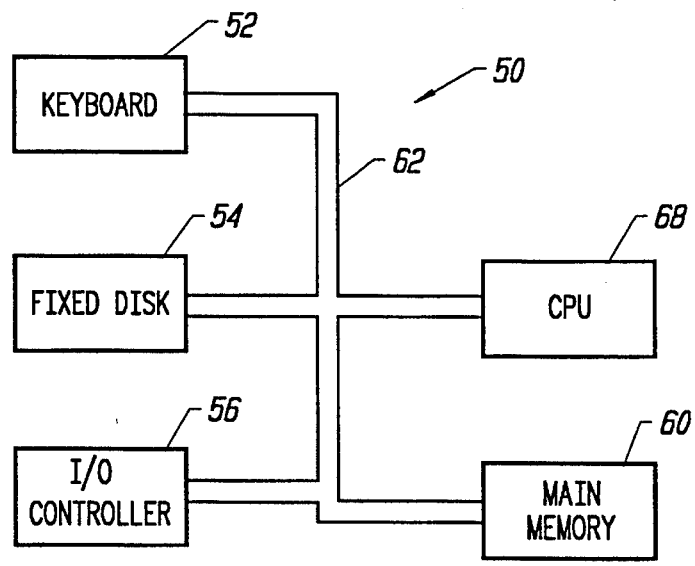
FIG. 2 is block diagram of a computer system suitable for use with the preferred embodiments of this invention.

The invention may be embodied on a digital computer system such as the system 50 of FIG. 2, which includes a keyboard 52, a fixed disk 54, a display monitor 54, an input/output controller 56, a central processor 58, and a main memory 60. The various components communicate through a system bus 62 or similar architecture. The user enters commands through keyboard 52; the computer displays images through the display 54, such as a cathode ray tube, liquid crystal display, printer, etc. Preferably, the display will provide high resolution graphical images of the molecular structures simulated according to this invention. In preferred embodiments, an appropriately programmed computer, such as a Silicon Graphics or Sun Microsystems workstation. Other computers, however, may be used in conjunction with the invention. Suitable computers include mainframe computers such as a VAX (Digital Equipment Corporation, Maynard, Mass.) or Cray Supercomputer (Cray Research), multiprocessor computers such as those produced by Thinking Machines (Cambridge, Mass.), workstations such as the Sun SPARC (Sun Microsystems, Sunnyvale, Calif.), personal computers such as Macintosh computers (Apple Computer, Cupertino, Calif.) or IBM or IBM compatible personal computers.

IV. Simulation of Protein Dynamics

A. Macromolecular Structure

A preferred embodiment of the invention involves simulations of macromolecule conformations and, in particular, peptide and protein conformations. A peptide is an oligomer of amino acids attached in a linear sequence to form, for example, a protein or an enzyme. Peptides consist of a main chain backbone having the following general pattern:

where n equals the number of amino acid residues in the peptide and $C^\alpha$ is the so-called alpha carbon of an amino acid. Attached to each alpha carbon is a distinctive side-chain that identifies each amino acid.

A peptide's structure may be described at various levels. The primary sequence of a peptide represents the sequence of the constituent amino acids. The peptide's secondary structure represents the complex shape of main chain and generally indicate structural motifs of different portions of the peptide. Common secondary structure includes, for example, alpha-helices, beta-sheets, etc. The tertiary structure of a peptide represents the three dimensional structure of the main chain, as well as the side-chains conformations. Tertiary structure may be represented by a set of coordinates that specify that positions of each atom in the peptide main chain and side-chains and is often visualized using computer graphics or stereopictures. Finally, quaternary structure represents the three-dimensional shape and the interactions that occur between different peptide chains, such as between subunits of a protein complex.

Non-amino acid fragments are often associated with a peptide. Such fragments can be covalently attached to a portion of the peptide or attached by non-covalent forces (ionic bonds, van der Waals interactions, etc.). For example, many peptides are bound in the cell membrane are used for cell recognition and have carbohydrate moieties attached to one or more amino acid side-chains. Non-amino acid moieties include, but are not limited to, heavy metal atoms such as, for example single molybdenum, iron, or manganese atoms, or clusters of metal atoms, nucleic acid fragments (such as DNA, RNA, etc.), lipids, and other organic and inorganic molecules (such as hemes cofactors, etc.).

The three-dimensional complexity of a peptide arises because some covalent bond angles in the peptide can bend and some bonds can rotate. The "conformation" of peptide is a particular three-dimensional arrangement of atoms and, as used herein, is equivalent to its tertiary structure. The large size of a peptide chain, in combination with its large number of degrees of freedom, allows it adopt an immense number of conformations. Despite this, many peptides, even large proteins and enzymes, fold in vivo into well-defined three-dimensional structures.

The peptide generally folds back on itself creating numerous simultaneous interactions between different parts of the peptide. These interactions result in stable three-dimensional structures that provides unique chemical environments and spatial orientations of functional groups that give the peptide its special structural and functional properties, as well as its physical stability. A preferred embodiment of this invention is directed to predicting peptide structures, and hence stabilities and functional properties, from knowledge of constituent amino acids. In addition, the invention is directed to predicting conformations of other macromolecules such as nucleic acids which fold or pack into preferred conformations.

In other preferred embodiments, the invention is directed to accurately predicting the motions of atoms in a peptide or macromolecule. The peptide molecule naturally moves between various stable conformations, and may deviate somewhat from an equilibrium structure under the influence of external forces such as those associated with a ligand.

Figure 3A:
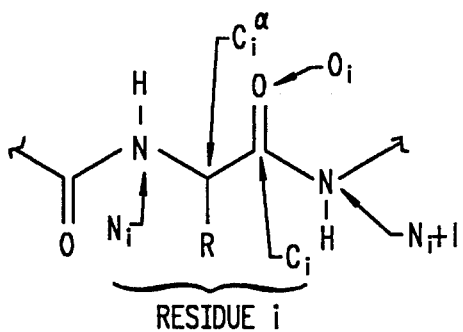
FIG. 3a is a schematic illustration of the atoms of an amino acid in a peptide.

Peptides fall into the general class of polymers and are simply molecules generated from a sequence of amino acid residues connected in series. With reference to FIG. 3a, the peptide backbone, or main chain, consists of a repeated sequence of three atoms: an amide nitrogen $N_i$, the alpha carbon $C_i^\alpha$, and the carbonyl carbon $C_i$, where i represents the amino acid in the peptide sequence. The carbonyl oxygen, $O_i$, is attached to the carbonyl carbon and hydrogens are attached to both the amide nitrogen and alpha carbon. In principle, rotation can occur around any of the three bonds of the peptide main-chain. In practice, however, the bond between $C_i$ and $N_{i+1}$, the peptide bond, has partial double bond character that inhibits its rotation and in the absence of a strong force; $C_i^\alpha$, $C_i$, $O_i$, and $N_{i+1}$ lie in approximately the same plane.

Figure 3B:
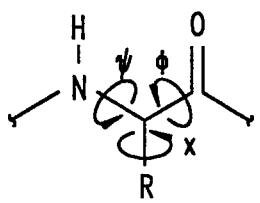
FIG. 3b is a schematic illustration of an amino acid residue showing the locations of the $\Psi$ and $\phi$ torsions, and one, $\chi$ torsion.
Figure 3C:
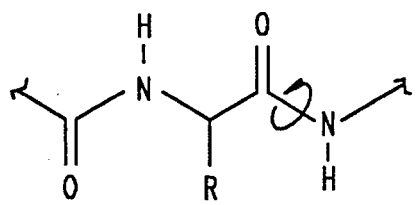
FIG. 3c is a schematic illustration of an amino acid residue showing the locations of an $\omega$ torsion.

A preferred method of determining peptide conformations and dynamics includes prediction of two basic classes of degrees of freedom. The $\Psi$ and $\phi$ (and sometimes $\omega$ torsions of the amino acids which determine the folding of main chain atoms of the peptide, and the $\chi$ torsions, which specify the set of angles that defines the conformation of each amino acid side-chains. These two sets of variables are closely coupled, because of the tremendous importance of side-chains conformation and packing for the stability of the overall peptide conformation. FIG. 3b shows the locations of the $\Psi$, $\phi$, and $\chi$ rotational degrees of freedom. The $\Psi$ torsion represents rotation about the bond connecting the amide nitrogen $N_i$ to the alpha carbon $C_i^\alpha$, the $\phi$ torsion represents rotation about the bond connecting the alpha carbon $C_i^\alpha$ to the carbonyl carbon $C_i$, and the first $\chi$ torsion represents rotation about the bond connecting the alpha carbon $C_i^\alpha$ to the side chain group R. Other $\chi$ torsions are important in amino acids having larger side-chains. A preferred method of the invention determines the set of favored $\Psi$, $\phi$, and $\chi$ torsional conformations. Some preferred embodiments also determine the $\omega$ angle (see FIG. 3c) between two adjacent amino acids.

Figure 4:
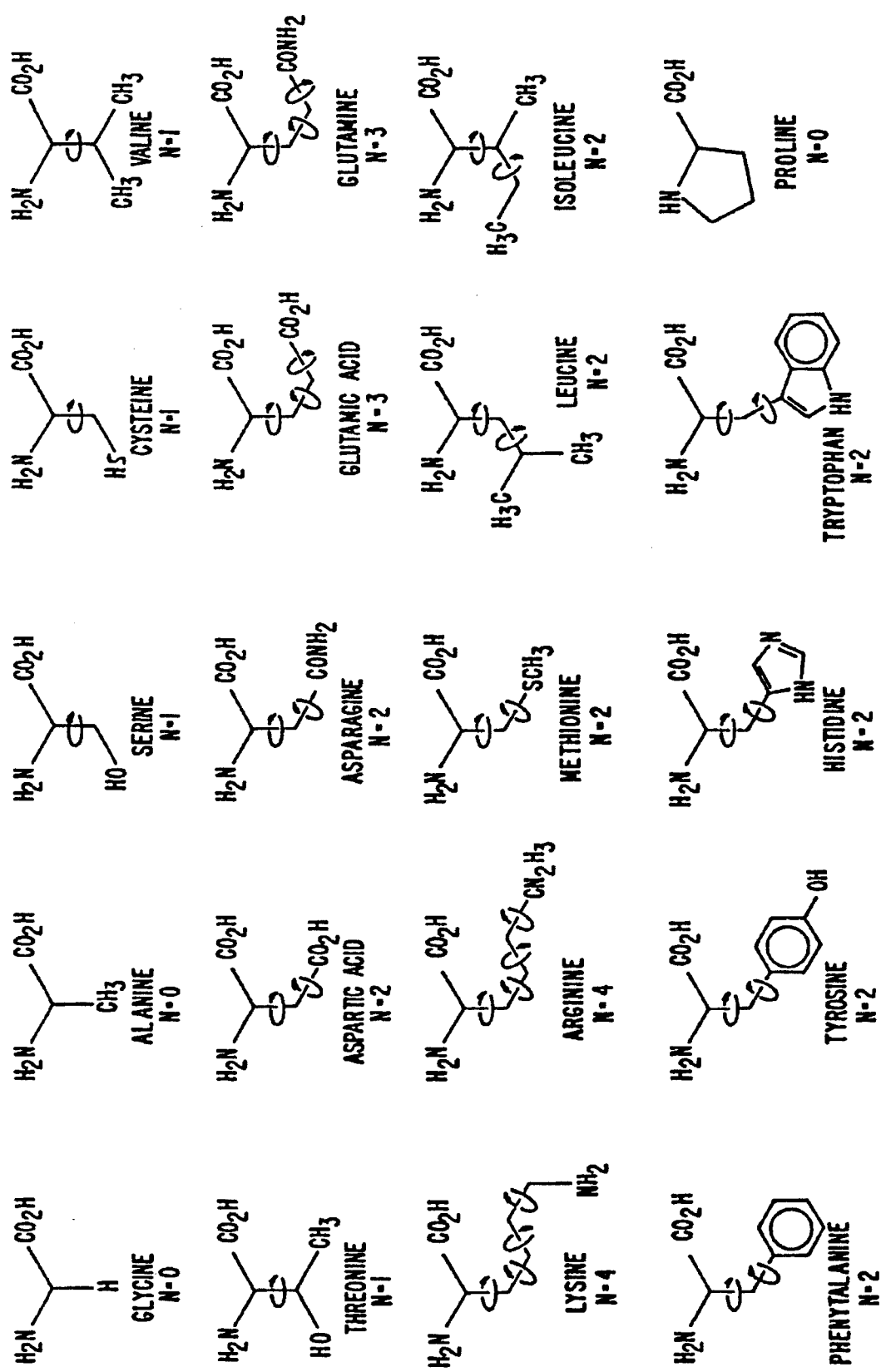
FIG. 4 shows preferred $\chi$ side-chain torsions used in simulations of molecular systems containing one or more of the twenty genetically coded amino acids.

There are twenty common naturally-occurring amino acids which have the general structures shown in FIG. 4. The individual side-chains (R)—which distinguish the amino acids—can adopt a myriad of possible conformations, the number of which depends on the number of predefined rotational degrees of freedom. FIG. 4 illustrates one set of rotational degrees of freedom ($\chi$ torsions) for each amino acid. The value "N" shown if FIG. 4 represents the number of important $\chi$ torsions in each amino acid. The $\phi$ and $\Psi$ torsions are not shown in FIG. 4 because they are identical for each amino acid (except proline which has limited $\Psi$ degree of freedom. Eighteen of the twenty amino acids conform to the general structures provided in FIGS. 3a–3c. However, glycine, the simplest amino acid, contains a hydrogen atom in place of the side-chain R, and proline contains a side-chain that links to the amide nitrogen ($N_i$) to form a five-member ring. The first carbon of the side-chains, which is attached to $C_i^\alpha$, is the beta carbon, $C_i^\beta$. Successive carbons in the side-chain are labeled, $C_i^\gamma$, $C_i^\delta$, etc.

Although only twenty amino acids are commonly used in vivo as protein building blocks, less common natural amino acids exist, as well as unnatural amino acids. Amino acids in these categories include enantiomers and diastereomers of the natural D-amino acids, oxyproline, cyclohexylalanine, norleucine, cysteic acid, methionine sulfoxide, ornithine, citrulline, omega-amino acids such as 3-amino propionic acid, 4-amino butyric acid, etc. All such amino acids can be incorporated into peptides by suitable methods known in the art, and the structure of a peptide having these uncommon amino acids can be determined when the structure and properties of the uncommon amino acids are known. Thus, as used herein, the term amino acid includes all natural amino acids encoded by the genetic code, as well as uncommon natural amino acids and unnatural amino acids.

In addition to determining peptide structure, the invention method is suitable for determining the structure of polydeoxyribonucleic acids (DNA) and poly-ribonucleic acids (RNA), as well as protein-DNA and protein-RNA complexes. The five common, naturally occurring nucleotides adenine, guanine, cytosine, thymine, and uracil have the general structure consisting of a phosphate, a sugar, and a purine or pyrimidine base. Each of these nucleotides is planar, and has one main rotational degree of freedom. In addition to the common, naturally-occurring nucleotides, oligonucleotides often contain other nucleotides such as Base Y, $N^2$-dimethyl guanosine, inosine, dihydrouridine, etc. Such nucleic acids are well known in the art (see, Canter et al. "Biophysical Chemistry, Part I" (1980), pg. 155, which is incorporated by reference for all purposes). As used herein, nucleotide refers to the set of common and uncommon naturally-occurring nucleotides, as well as the set of unnatural nucleotides. In all such nucleotides, the sugar ring may be deoxyribose, ribose, or any suitable variation (such as, for example, in a 2-methyl nucleotide).

B. The Initial Conformation

As noted, there may be considerable latitude in setting the initial conformation of the peptide or other molecular representation. When the initial conformation of the representation is set reasonably close to the actual conformation, considerable computational savings may be realized. In some embodiments, a partial three-dimensional structure of the peptide may be used as a starting point for the simulation. For example, the peptide being simulated may have already been synthesized and studied, or it may be closely related to a peptide for which the structure is already known. In either case, some but not all structural information may be available to guide the initial conformation of the representation. Many suitable methods exist that provide this partial information. X-ray or neutron diffraction (hereinafter referred to as "diffraction") provides a detailed picture of the three-dimensional positioning of the peptide main chain. Diffraction methods are well known (see, for example, Cantor et al. "Biophysical Chemistry Vol. III" (1980) W. H. Freeman & Co., San Francisco, chapter 13, which is incorporated by reference for all purposes).

Other methods for partially determining the three-dimensional conformation of the peptide suitable for use with the invention include, for example, nuclear magnetic resonance (NMR) spectroscopy and theoretical prediction. Suitable NMR methods include, for example, one-dimensional proton ($^1$H) NMR spectroscopy, which is used to identify individual protons in a peptide, two-dimensional $^1$H NMR methods (including correlated experiments which rely on J-coupling) which provide interproton relationships using through-bond coupling, and the Nuclear Overhauser Effect (NOE) experiments which provide spatial relationships using through-space information (see Griesing et al. J. Mag. Res. (1989), vol. 73, pg. 574. which is incorporated by reference for all purposes.) Other NMR methods suitable for use with the present invention are well known in the art (see Lecome, "NMR/X-Ray Workshop: An Overview" in "Techniques in Protein Chemistry II" (1991), pg. 337, Academic Press, Inc., San Diego, which is incorporated by reference for all purposes).

Figure 5:
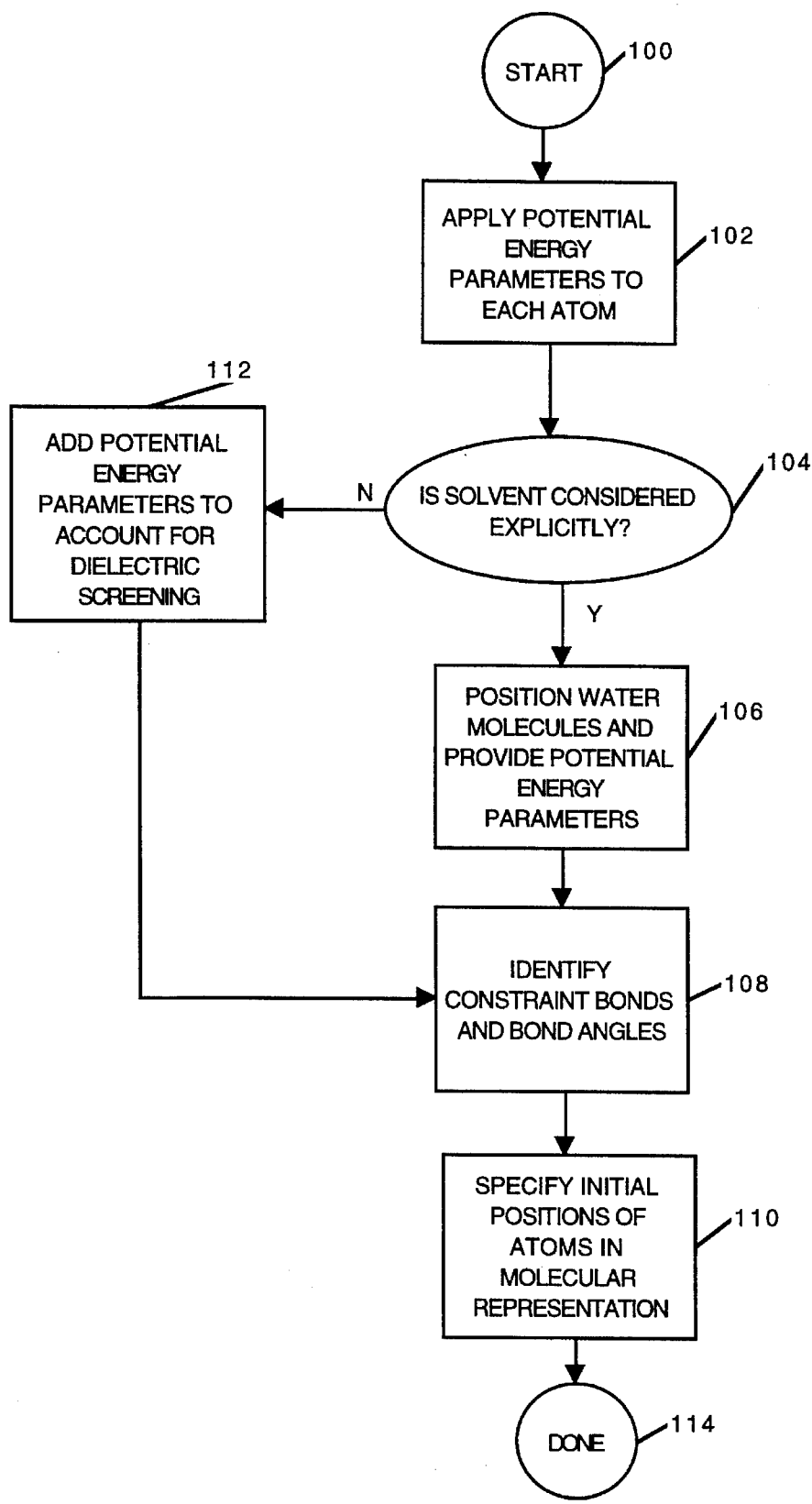
FIG. 5 is a process flow diagram showing preferred process steps employed in setting up molecular representations in accordance with this invention.

The process of setting up the initial parameters and conformations of the molecular representation (step 6 of FIG. 1 ) is detailed in FIG. 5. The process begins at 100 and proceeds to a step 102 where the potential energy parameters are applied to each atom of the representation. These may be van der Waals radii, electrostatic partial charges, dielectric screening constants, etc. as explained below. Usually, the values associated with the parameters will depend upon, at least, the element (carbon, nitrogen, oxygen, etc.), and often the particular residue in which the atom resides. After the potential energy parameters have been applied to each atom, a decision step 104 determines whether solvent is to be explicitly considered in the simulation. If so, the water molecules associated with the simulation must be added to the peptide molecule. This may involve treating the water molecules as either unitary objects or compounds containing an oxygen and two hydrogen atoms as described below. In either case, potential energy parameters analogous to those applied to the atoms of the peptide are applied to the water molecules of the representation. Next, a step 108 identifies the constraining bonds and bond angles of the representation. In preferred embodiments, these remove all degrees of freedom except the peptide's $\Psi$, $\phi$, and $\chi$ angles, and in some cases the $\omega$ torsion angles. From this information, an initial conformation of the molecular representation can be set. The values associated with the $\Psi$, $\phi$, $\chi$, and $\omega$ angles can be set randomly or in accordance with known structural information as discussed above. Thereafter, the process is completed at 114.

If decision step 104 determines that the solvent is not to be explicitly considered in the representation, the effect of the solvent must be included in some other manner. This is accomplished in a step 112 which adds appropriate potential energy parameters to account for the solvent effect on the interatomic potentials between the atoms of the representation. This might include, for example, adding a dielectric screening parameter to certain terms of the potential energy expressions of the molecular representation as explained below. After step 112 is complete, the system proceeds to step 108 whereupon the process is completed as described above.

In preparing the initial conformation of the representation, the identity of each atom in the peptide must be specified.

This information it provided by the primary sequence of a peptide which represents the identity and sequence of the peptide's amino acids and may be obtained by techniques well-known in the art of peptide chemistry and molecular biology. Suitable methods for determining the primary sequence include, but are not limited to, direct determination from X-ray crystal data, peptide sequencing, and gene sequencing.

As noted, various covalent distance constraints ("$l_{ij}$") are imposed on the atoms of the representation. Angle constraints are put in by combining a number of distance constraints. To constrain the angle $\angle r_i r_j r_k$, where the lengths $l_{ij}$ and $l_{jk}$ are constrained, one simply constrains the length $l_{ik}$ and effectively introduces an artificial bond length constraint. In addition to bond length and bond angle constraints, the present invention may employ planar constraints. This becomes necessary in peptides because the carbonyl carbon and oxygen, $C^\alpha$, and the amide nitrogen are generally constrained to lie in a plane. As explained below, the planar constraints are put in by using dummy atoms located above and/or below the plane.

For each amino acid, regardless of identity, the constraints are preferably defined in terms of 6 sub-residue units. These include Nitrogen (N), Carbon-Hydrogen ($C^\alpha H$), and Carbon (C), with a Hydrogen (H) attached to the N and an Oxygen (O) attached to the C. The first atom of the side chain ($C^\beta$) is attached to the $C^\alpha H$ and is considered to be one unit. Other units of the side-chain will vary for each amino acid, but they can readily be determined based upon the principles described herein. The positions of the atoms are labeled in terms of the following:

H: $r_1^{(a)}$

N: $r_2^{(a)}$ $C^\alpha H$: $r_3^{(a)}$ $CH_3$: $r_4^{(a)}$

C: $r_5^{(a)}$

O: $r_6^{(a)}$ where the integer index a denotes the amino acid. The following constraints are then imposed on each amino acid residue in the molecular representation:

$$(l_{ij}^{(ab)}=|r_i^{(a)}-r_j^{(b)}|):l_{12}^{(\alpha\alpha)},l_{13}^{(\alpha\alpha)},l_{23}^{(\alpha\alpha)},l_{24}^{(\alpha\alpha)},l_{25}^{(\alpha\alpha)},l_{34}^{(\alpha\alpha)},$$
$$l_{35}^{(\alpha\alpha)},l_{36}^{(\alpha\alpha)},l_{45}^{(\alpha\alpha)},l_{56}^{(\alpha\alpha)},l_{32}^{(\alpha\alpha+1)},l_{43}^{(\alpha\alpha+1)},l_{52}^{(\alpha\alpha+1)}.$$

These constraints take care of all the bond lengths and most of the bond angles in the system. However, in preferred embodiments, all motion is constrained except for the two dihedral angles ($\phi^{(a)},\varphi^{(a)}$) per amino acid and perhaps the $\omega^{(aa+1)}$ angle, defined between two neighboring amino acids. The above constraints do not maintain the $H^{(a)}$ in the plane defined by ($N^{(a)}$, $C^\alpha H^{(a)}$, $C^{(a-1)}$). This can be obtained by introducing two dummy atoms per amino acid. Denoting these atoms by $D_1^{(\alpha)}$ and $D_2^{(\alpha)}$ and their positions by $r_0^{(\alpha)}$ and $r_7^{(\alpha)}$ the H and the O can be constrained in the two following ways:

Constraining the ω Angle: $l_{01}^{(\alpha\alpha)},l_{02}^{(\alpha\alpha)},l_{03}^{(\alpha\alpha)},l_{73}^{(\alpha\alpha)},l_{75}^{(\alpha\alpha)},l_{76}^{(\alpha\alpha)},l_{71}^{(\alpha\alpha+1)},l_{72}^{(\alpha\alpha+1)},l_{73}^{(\alpha\alpha+1)}$. Counting the total number of constraints and subtracting this number from the total number of degrees of freedom in the system leaves $6+2N_a$, where $N_a$ the number of amino acids. This is the number of degrees of freedom in the constrained system and consists of 3 for the center of mass, 3 for the Euler angles, and the two dihedral angles ($\phi,\varphi$) for each amino acid.

Flexible ω Angle: Counting the total number of constraints and subtracting this number from the total number of degrees of freedom in the system leaves $5+3N_a$. This number represents 3 for the center of mass, 3 for the Euler angles, the two dihedral angles ($\phi,\varphi$) for each amino acid, and the ω angles between the amino acids.

C. The Interatomic Non-Covalent Potential

In the methods of this invention, non-bonding interatomic forces are determined for each atom in the molecular representation at each time step (step 8 of FIG. 1 ). This is accomplished by adding the force vectors due to the various atoms surrounding the atom under consideration. In preferred embodiments, the force vectors are determined by differentiating interatomic potential energy expressions with respect to distance vectors between the atom under consideration and the other atoms of the representation contributing to the interatomic potential.

The conformation energy of a peptide or other molecular system can be modeled in many ways, ranging from potential energy functions having a single van der Waals interaction term, to potential energy functions having many terms that account for torsional biasing, electrostatic interactions, hydrogen bonding, hydrophobic interactions, entropic destabilization, cystine bond formation, and other effects.

The van der Waals force is an electrostatic interaction arising from an instantaneous asymmetric electron distribution, which causes a temporary dipole. This transient dipole induces a complementary dipole in a neighboring atom to stabilize the transient dipole. An instant later the dipoles are likely to be reversed resulting in an oscillation and a net attractive force. At one extreme (as the interatomic distance tends to infinity), atoms do not interact and have no stabilizing or destabilizing effect on one another. At the other extreme (as interatomic distance tends to zero) the electrostatic repulsion between atoms becomes strong and dominates other stabilizing effects. The potential becomes infinite, which physically corresponds to superimposing two atoms. Sometimes it is desirable to explore conformation space that is otherwise blocked by this infinite energy barrier. This is especially true when very little information is initially known about the molecular system's conformation. Various techniques may be employed to overcome the energy barrier and allow a full exploration of conformation space. In one preferred approach, the magnitudes of the random thermal noise forces are increased (this is analogous to raising the temperature) when a greater range of conformation space is to be explored. Alternatively, the energy barrier can be truncated if it reaches a predefined magnitude.

As is well known, the force between two charges of the same sign is repulsive while the force between charges of opposite signs is attractive. This type of electrostatic interaction has the greatest influence on charged residues, such as lysine, arginine, glutamic acid, aspartic acid, etc. Inclusion of an electrostatic energy term requires assignment of a charge to each atom. As is well known in the art, the effective charge of an atom depends on its surrounding environment including such factors as, for example, pH, accessibility to water, the polarity of the solvent, and the presence of other charges.

Other types of electrostatic forces influence peptide structure as well. For example, permanent dipole moments, which describe partial charges on an atoms, occur in an uncharged, but polar groups of atoms. The electrostatic potential described by such dipole moments are well known and may be implemented as is known in the art. Another type of primarily electrostatic interaction is the hydrogen bond, which occurs when a hydrogen atom is shared between a proton donor and a proton acceptor. Hydrogen bonds stabilize pairs of polar moieties having hydrogen atoms to share and donate, such as between a serine hydroxyl group and the carbonyl carbon of an amide group, or between acid group such as the carboxyl of a glutamic acid and water. The potential energy terms for both dipole and hydrogen bond interactions are well known in the art (see Cantor et al.).

Hydrophobic interactions are destabilizing noncovalent interactions between an atom having hydrophilic character and one having hydrophobic character. For example, large hydrophobic interactions occur between the polar, aqueous environment of the solvent and nonpolar residues of the peptide, such as valine, leucine, isoleucine, phenylalanine, etc. As applied to prediction of side-chains conformations, hydrophobic interactions result in a tendency for nonpolar side-chains to avoid interaction with solvent. Potential energy functions representing hydrophobic interactions are well known in the art and are used in some preferred embodiments to increase the prediction accuracy of hydrophobic side-chains that happen to be exposed to solvent on the surface of the peptide.

Other forces exist between atoms of the peptide. For example, a torsional potential energy function models the interaction of linear four-atom sequences, such as Y—C—C—X. (See Streitwiser et al. "Organic Chemistry," 2d ed., Wiley & Sons, pg. 70 (1987) for a description of torsions about a carbon-carbon single bond). One approach to modeling torsional forces and incorporating it with non-bonding interatomic forces is described below. Still other energetic terms influence the overall conformation of a peptide and contribute to the overall potential energy function (see, for example Dill Biochemistry (1990), Vol. 29, pg. 7133, which is incorporated by reference for all purposes). For example, entropic terms, which account for the decrease in rotational and other degrees of freedom in the transition from unfolded to folded peptide are suitable for inclusion into the conformational energy calculation.

Figure 6:
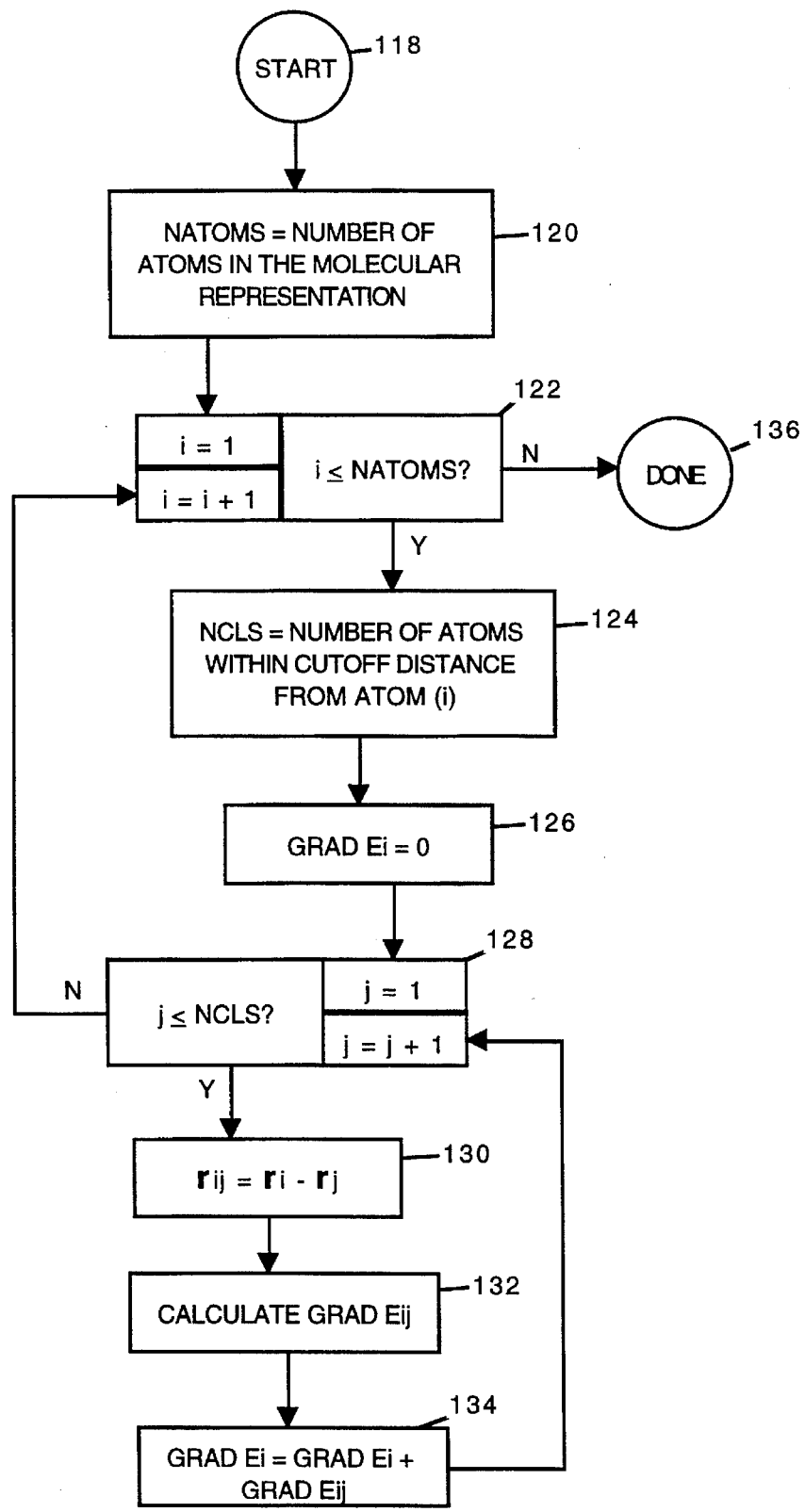
FIG. 6 is a process flow diagram depicting a preferred process for determining the interatomic non-bonding forces (grad E) associated with the atoms of the representation.

A preferred approach to determining the interatomic non-covalent force is depicted in FIG. 6 (corresponding to step 8 of FIG. 1). The process begins at 118 and proceeds to a step 120 where the variable NATOMS is set equal to the number of atoms in the molecular representation. This will typically be the number of atoms in the molecular system being represented, but may in some instances be less than the total number of atoms. The remainder of the process is spent determining the interatomic potentials experienced by each atom. An iterative loop step 122 initializes an atom counter "i" to one and also determines whether the current value of i is less than or equal to NATOMS. If it is, a process step 124 sets the variable NCLS equal to the number of atoms within a cut-off distance from atom(i), the atom under consideration. The cut-off distance is a predefined distance away from the atom under consideration. In theory, every atom in the molecular system contributes to the interatomic potential experienced by each single atom in the system. However, when the distance between the atom under consideration and another atoms becomes sufficiently great, the potential caused by the other atom is negligible. Thus, in preferred embodiments, only certain atoms—those within the predefined cut-off distance—are considered in determining the interatomic potential for a given atom under consideration.

After step 124, the gradient of potential for the atom under consideration, $\nabla E_i$, is initialized to zero. Thereafter, an iterative loop step 128 initializes a counter "j" to one and determines whether j is less than or equal to the value NCLS. If it is, a step 130 determines the distance vector $r_{ij}$ between the atom under consideration (atom(i)) and a second atom (atom(j)). This is accomplished by simply subtracting the Cartesian position of $r_i$ from that of $r_j$. Thereafter, a step 132 calculates the value of $\nabla E_{ij}$, the interatomic force vector between atoms i and j. This is typically accomplished by differentiating the energy function for the interatomic potential with respect to vector $r_{ij}$. Next, a step 134 adds the contribution from $\nabla E_{ij}$ to the value of $\nabla E_i$. Process control then returns to iterative loop step 128 where the counter j is incremented by one. Steps 130, 132, and 134 are then repeated for the atom under consideration (atom(i)) and a different atom within the cut-off distance from atom(i). This is continued until every atom within the cut-off distance of atom(i) has been considered and its contribution to $\nabla E_i$ included. At that point, iterative loop step 128 determines that the value of j is no longer less than or equal to NCLS, and process control returns to iterative loop step 122 where i is incremented by one. In other words, another atom in the molecular representation is selected and the interatomic non-covalent forces it experiences are determined. As before, step 124 sets the value of NCLS, step 126 initializes $\nabla E_i$ to zero, and steps 128, 130, 132, and 134 determine the interatomic force experienced by atom(i). Iterative loop step 122 directs the process to consider each new atom(i) until the last atom in the molecular representation have been treated. The process is then finished at 136.

In a preferred embodiment of the invention, the interatomic potential energy used to calculate $\nabla E_{ij}$ (step 132 of FIG. 6) is modeled by an energy function combining van der Waals and electrostatic energy terms given by the OPLS pair potentials:

$$\tilde{E}_{ij}(r_{ij}) = \frac{q_i q_j}{\epsilon(r_{ij})r_{ij}} + \frac{\sqrt{A_i A_j}}{r_{ij}^{12}} - \frac{\sqrt{B_i B_j}}{r_{ij}^{6}} \quad (3)$$

where the parameters $q_i$, $A_i$, and $B_i$ are given for the ith atom. A screening function $\epsilon$ reflects the dielectric nature of the solvent as well as the peptide itself. Various dielectric screening functions may be employed as is known in the art. Alternatively, local electric fields may be computed and used to estimate position dependent screening as discussed in the following references: Jean-Charles et al., J. Am. Chem. Soc., 113:1454–5 (1991) and Sharp et al., J. Phys. Chem., 94:7684–92 (1990), both of which are incorporated herein by reference for all purposes. In a preferred embodiment, the dielectric functional form is given by the following expression:

$$\epsilon(r) = \exp(r/3) \quad (4)$$

The value of r is measured in units of one Å. The particular values for the q, A, and B parameters vary depending upon the particular atom (oxygen, nitrogen, carbon, etc.) and the residue in which the atom occurs. The OPLS pair potentials are described in Jorgensen, et al., *Journal or the American Chemical Society*, 110:1657–1666 (1988) which is incorporated herein by reference for all purposes. There are up to 54 different OPLS pair potentials provided for the atoms of a protein.

Preferably, only those atoms within a predefined cutoff distance from one another will contribute the interaction potential. This cutoff distance may vary depending upon the molecular system being studied. In a study of poly-alanine, it was found that a preferred cutoff distance was about 10Å. Generally, however, cutoff distances between about 6 and 15Å should work. Much longer cutoff distances are permissible when the coulombic forces (potentials) are expressed as multi-pole expansions.

In order to smooth the transition at the cutoff region, the OPLS pair potentials expression may be modified to give the following:

$$E_{ij}(r_{ij}) = [\tilde{E}_{ij}(r_{ij}) - \tilde{E}_{ij}(r_c)] \left(1 - \left(\frac{r_{ij}}{r_c}\right)^n\right)^m, r_{ij} < r_c \quad (5)$$

$$E_{ij}(r_{ij}) = 0, r_{ij} \geq r_c \quad (6)$$

where the OPLS potentials are denoted by $\tilde{E}_{ij}$. The cutoff distance is $r_c$ and two additional smoothing parameters are m and n. m denotes the order of the zero at $r_{ij}=r_c$ for the force and n determines at which distance the smoothing is turned on. In preferred embodiments, the value of m is about 3 and the value of n is about 18.

D. Frictional Forces and Noise

As noted, the high frequency motions in a molecular system are replaced by the noise forces, N, which are balanced at a given temperature, T, by corresponding frictional forces represented by the matrix $\Xi$. Actually, the elements of the friction matrix multiplied with the velocity vector give the frictional forces. The friction terms account for two effects: (1) the interactions between the atoms of the molecular system and a solvent, and (2) the vibrations within the molecular system itself. In general, the frictional forces associated with the molecular system are correlated from atom to atom in the simulation. These effects can be easily introduced through the Oseen tensor and include off-diagonal elements in the matrix $\Xi$. See, e.g., Rotne et al., *J. Chem. Phys.*, 50:4831 (1969) which is incorporated herein by reference for all purposes. However, it is often sufficient to assume that the friction (and noise) is uncorrelated, in which case the matrix $\Xi$ reduces to a diagonal matrix $\gamma\xi 0$ where $\xi 0$ is the friction constant. By assuming that all atoms have the same effective radius in interaction with the solvent (e.g., $a_i$=3Å), the friction constant may be given by $\xi 0 = 6\pi\xi a_i$ (Stoke's Law), where $\xi$ is the viscosity of the solvent ($\xi$=0.9 cp for water).

When it is desired to treat the friction between the different parts of the molecule as correlated (through the velocity field of the solvent), $\Xi$ may be generalized by introducing the Oseen tensor in terms of the inverse friction matrix, $\Xi^{-1} = \{\upsilon_{ij}\}$ in the following form, where $\upsilon_{ij}$ is a 3×3 matrix:

$$\upsilon_{ij,mn} = (6\pi\xi\alpha_i)^{-1}\delta_{mn}, i=j \quad (7)$$

$$\upsilon_{ij,mn} = (8\pi\zeta|r_i - r_j|)^{-1} \times \left[\delta_{mn}\left(1 + \frac{1}{3}\frac{a_i^2 + a_j^2}{|r_i - r_j|^2}\right) + \frac{(r_i - r_j)(r_i - r_j)^T}{|r_i - r_j|^2}\left(1 - \frac{a_i^2 + a_j^2}{|r_i - r_j|^2}\right)\right], \quad (8)$$

$$i \neq j$$

where m, n denotes the coordinates in the 3×3 blocks and $\delta_{mn}=1$ for m=n and $\delta_{mn}=0$ for m≠n. The viscosity of the surroundings is given by $\xi$ and the interaction radius of the ith atom is denoted by $a_i$.

The thermal noise term, N, employed in this invention represent (1) Brownian motion from solvent molecules, plus (2) the covalent forces of the atom coupled at high speed. This invention treats these forces as essentially random over a long time. The particular value chosen for the random force is given by a random number generator with a gaussian distribution. The noise terms are chosen in such a way as to guarantee that an ensemble of initial points will tend to a Boltzmann distribution $P(E) \propto \exp(\beta E(\{x_i\}))$ on integrating Eq. (1) over sufficiently long times. It may be verified, as expected, that the equations (1) lead asymptotically to a Boltzmann distribution provided the noise forces on each particle remain uncorrelated. However, if the noise spectrum is generalized to include inter-atomic correlations, then $\Xi$ would have to be further modified to guarantee the Boltzmann distribution as $t \to \infty$.

Figure 7:
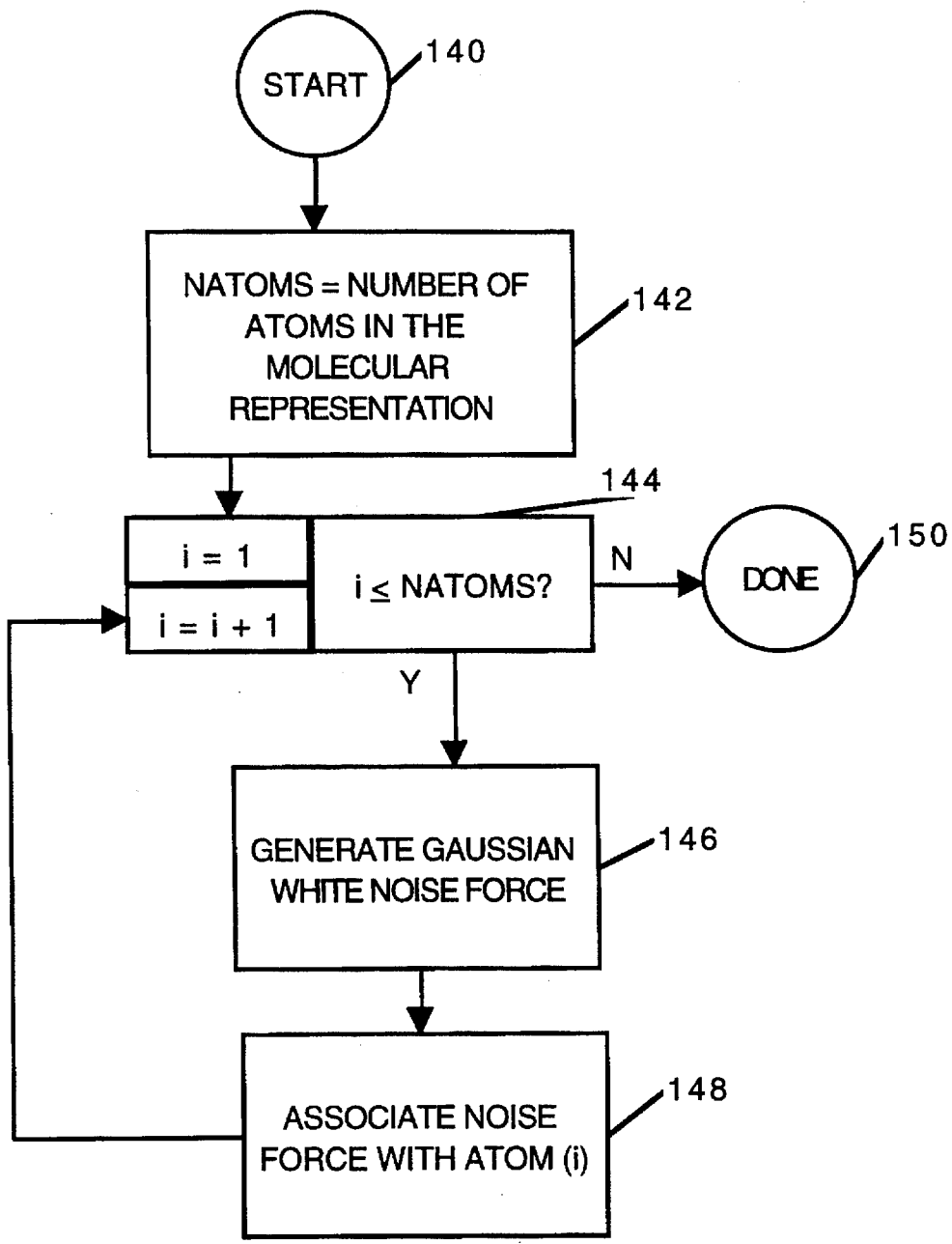
FIG. 7 is a process flow diagram depicting a preferred process for determining the thermal noise forces associated with the atoms of the representation.

The steps of providing a thermal noise force to each atom are shown in FIG. 7 (corresponding to step 12 of FIG. 1). The process begins at 140 and proceeds to a step 142 where the variable NATOMS is set equal to the number of atoms in the molecular representation. Thereafter, an iterative loop step 144 initializes an atom counter i to one and determines whether the current value of i is less than or equal to NATOMS. If so, a step 146 generates a random noise force. The distribution of noise force magnitudes will follow a gaussian white noise distribution. The random noise force so generated is then associated with atom(i) in a step 148. Process control thereafter returns to iterative loop step 144 where atom counter i is incremented by one. Then, process steps 146 and 148 are repeated for the new atom. This continues until every atom in the representation has been considered and given a random noise force. At this point, i is no longer less than or equal to NATOMS, and the process is completed at 150.

E. The Constraint Forces

As noted, the forces acting to move the atoms of the molecular representation (i.e., the non-covalent forces and the thermal noise forces) will have a components in the direction of each constraining force on the atoms. This invention removes these components from consideration in the solution of the Langevin force balance (except in the rare instance when it is unnecessary because the constraining force is orthogonal to the resultant force). That component of force which tends to alter a constrained bond length (or bond angle or peptide bond planarity) is projected out analytically through the constraint force vector S.

Those forces that are trying to change the constraints are removed by projecting them out of the force expression. By "projecting out," it is meant that component is removed by vector subtraction. So the new force no longer pushes in the direction of the constraining force (i.e., the atom no longer feels a piece of the force along the constraint direction). As shown by Eq. 2, the constraint vector S includes coefficients $s_{ij}$ which will vary depending upon the magnitude of the interatomic non-bonding and thermal noise forces. Thus, the $s_{ij}$ must be recalculated for each time step, as the values of the other forces will change.

The values of $s_{ij}$ can be found by solving the following linear system of equations:

$$(r_l - r_k)^T \sum_j (\upsilon_{ij} - \upsilon_{kj}) \sum_i s_{ji}(r_i - r_j) = -(r_l - r_k)^T \sum_j (\upsilon_{ij} - \upsilon_{kj})(-\nabla_j E + \eta_j) \quad (9)$$

where the $\upsilon_{ij}$ are elements of the inverse of the friction matrix, $\Xi^{-1}$. The constraints, $(r_j-r_k)$, are, for example, the bond length and bond angle constraints listed above as $l_{01}$, etc. In the simple case where the friction matrix is a diagonal matrix having constant terms, the $\upsilon_{ij}$ elements disappear. Given the positions of the atoms (which are available anew for each time step), the constraint forces given by $s_{ij}$ can be calculated. Although not particularly important to the practice of this invention, Eq. 9 can be derived by differentiating the constrained distance (bond length or angle) $l_{kl}=r_l-r_k$ with respect to time and inserting the result into Eq. 1. Solving the set of q linear equations (Eq. (9)), where q is the number of constraints in the system, gives the values for the $s_{ij}$'s. This can be accomplished by various matrix operations well known to those of skill in the art. Generally, the $s_{ij}$ can be found as a solution to a banded matrix equation, where the band thickness is given by the constraint between two atoms with the largest separation along the peptide chain.

A peptide can be viewed as series of oblong plates connected to one another by hinge angles. The "plates" are the peptide bonds (—N(H) C(O)—) which define a plane and the "hinge angles" are the φ and Ψ angles of the amino acids. In preferred embodiments, the system employs dummy atoms to constrain groups of four or more coplanar atoms in a single plane. Without such dummy atoms, the atoms making up the plane would tend to drift away from their equilibrium coplanar arrangement during movement. Before the first time step, dummy atoms are placed above and below the plane in a tent-like orientation. The specific location of the dummy atoms with respect to the atoms in the plane is set to maintain the planar conformation. Using the above notation, one can constrain the planarity of a peptide bond by constraining all the distances $l_{id}$, where i is the label of an atom in the plane and d is the label of the dummy atom. The dummy atoms act directly on each atom in the plane but have no interaction with other atoms in the system.

F. Evaluating the Overdamped Langevin Dynamics Expression

With each new time step, the values of N, S, Ξ, and ∇E are determined. This information is then used to set up and integrate a Langevin force balance to determine new locations of the atoms in the representation (steps 16 and 18 of FIG. 1). As noted, the use of an overdamped Langevin dynamics expression has several advantages. By treating the covalent forces as constraining forces and introducing noise and frictional forces, the molecular system's fast motions (of the order femtoseconds) need not be treated explicitly. In this manner, the slower motions (of the order picoseconds) such as rotational isomerization limit the size of the time steps. Thus, larger time steps and faster evolution of the molecular dynamics simulation results. Another advantage derives from treating the slower motions of the molecular system as overdamped. The frictional terms dominate in overdamped systems, thus preventing the system from oscillating and allowing the acceleration terms to be dropped. Without acceleration terms, the force balance reduces to a first order expression which can be evaluated without iteration. There is experimental evidence showing that protein motions on the slower time scales (i.e., greater than about 1 picosecond) are in fact overdamped. See, for example, Kottalam et al., *Biopolymers*, 29P1409–1422 (1990) and Kitao, et al., *Chemical Physics*, 158:447–72 (1991).

The overdamped Langevin expression provides a velocity term (R of Eq. 1) which is, of course, the time derivative of position. When the Langevin expression is rearranged to include this velocity as the only term on one side of the equation (see the second version of Eq. 1 above), the expression can be integrated numerically. Various techniques for numerical integration are known in the art. These include Euler's method and the Runge-Kutta method. In a preferred embodiment of this invention, a second order Runge-Kutta method is employed. The size of the time step employed in the integration will depend upon various factors, most notably the nature of the function being integrated. Generally, it will be desirable to use large time steps so that the motions of the molecular system can be studied over a large time regime. However, if the time steps are too large, the integration method will not resolve subtle features of the force functions and will thus not converge. Further, larger time steps tend to introduce errors into the constrained bond lengths. It has been found that time steps between about 0.5 and 10 picoseconds work well with the preferred embodiment. It should be noted that the time step can vary in size over the course of a simulation, although it will generally be easier to implement a constant time step.

Preferably the parameters employed in evaluating the Langevin dynamics expressions are provided as quantities in normalized units. For example, energy may be normalized to $E_0=10^3$cal/mol, temperature to $T_0=E_0/k_B\approx505K$, $k_B$ being the Boltzmann constant, and time to $\tau=\xi_0 r_0^2/E_0$, where $\xi_0$ is the characteristic friction and $r_0=1Å$ is the characteristic length.

G. Introducing the Effect of Water

As noted, it is often necessary to include the effects of water (or other solvent) because of the dipolar screening role of water, and because of entropic contributions to hydrogen bonding forces. In some cases, it may even be necessary to include water molecules in simulation explicitly (as when the kinetics of protein folding are to be accurately described). This involves setting up the initial conformation with various water molecules (each having three dimensional coordinates, conformations, and OPLS parameters) interspersed around the peptide molecule at appropriate locations. However, for applications where one wants a fast way to explore conformational space rather than study the kinetics, the water molecules need not be considered explicitly. In this case, the dielectric screening effect of water can be included by simply modifying interatomic potentials so that the effects of solvent are included within a two body approximation. For example, the dielectric function ε (used in Eq. 3) together with the hydrodynamic friction matrix can account, at least in part, for the solvent surrounding the peptide.

If water molecules are represented explicitly in the model, one can omit both the dielectric function and all the off diagonal elements in the friction matrix Ξ, or at least those representing the hydrodynamically induced correlations. However, when water molecules are to be treated explicitly, all forces (friction, noise, non-bonding interatomic, and constraining) associated with the each water molecule will have to be treated as they axe in a peptide as explained above. Generally, it is preferable to restrict the H—0 distances as well as the angle ∠HOH to fixed values. Denoting the positions of the three atoms by $r_{H1}$, $r_{H2}$, and $r_O$ the equations of motion can be written as follows:

$$\xi_{H1}\dot{r}_{H1}=-\nabla_{H1}E+\eta_{H1}+s_{OH1}(r_O-r_{H1})+s_{H1H2}(r_2-r_{H1}) \quad (11)$$

$$\xi_{H2}\dot{r}_{H2}=-\nabla_{H2}E+\eta_{H2}+s_{OH1}(r_O-r_{H2})+s_{H1H2}(r_{H1}-r_{H2}) \quad (12)$$

$$\xi_0\dot{r}_O=-\nabla_O E+\eta_O+s_{OH1}(r_{H1}-r_O)+s_{OH2}(r_{H2}-r_O) \quad (13)$$

where ξ is a scalar. The three constraints, $l_{OH1}^2=|r_O-r_{H1}|^2$, $l_{OH2}^2=|r_O r_{H2}|^2$, and $l_{H1H2}^2=|r_{H1}-r_{H2}|^2$, then determine the constraints through Eq. (9). In this case, where the molecule is very simple, this can be done by solving three linear equations with three unknowns, $s_{H1H2}$, $s_{OH1}$, and $s_{OH2}$. When these axe found, Eqs. (11)–(13) can be evolved in time. As described above, all the interactions with the surrounding atoms, water and peptide(s), are contained in the dynamical force terms (–∇E, as well as the thermal noise).

H. Torsion Forces

Bond angle or torsion forces may be included in the equations of motion described above. The torsion forces may be written in terms of the Cartesian coordinate forces and then be included in the force term –∇E in Eq. (1). For example, consider the angie ω, given by the four positions, $r_0$, $r_1$, $r_2$, and $r_3$, where the following distances are constrained: $l_{01}, l_{02}, l_{12}, l_{13}$, and $l_{23}$ (see the above notation). This system has 7 degrees of freedom, 3 for the center of mass, 3 for the Euler angles, and 1 being the angle ω of the bond $l_{12}$. The angle may be defined as follows:

$$X_1=(r_1-r_0)\times(r_2-r_1)$$

$$Y_1=X_1\times(r_2-r_1)$$

$$X_2=(r_2-r_1)\times(r_3-r_2)$$

$$Y_2=X_2\times(r_2-r_1)$$

From these vectors, ω is defined by, $$\cos\omega = \frac{X_1^T \cdot X_2}{|X_1||X_2|}$$

$$\sin\omega = \frac{X_1^T \cdot Y_2}{|X_1||Y_2|}$$

If there is a bond torsion potential V(ω), the torsion force Γ is then given by $\Gamma=V^1(\omega)$. In the Cartesian coordinates, this force can be realized as follows. Let $f_i$ denote the force contribution on the ith particle to give the following torque conditions:

$$\Gamma_{X1}=0$$

$$\Gamma_{Y1}=0$$

$$\Gamma_{X2}=0$$

$$\Gamma_{Y2}=0$$

$$\Gamma_{r12}=\Gamma$$

It is further required that, $$\sum_{i=0}^{3} f_i = 0$$

and selecting, $$f_0 \| X_1$$

$$f_3 \| X_2$$

determines all the Cartesian forces $f_i$ describing the torsion force Γ along the $r_{12}$ axis. The forces $f_1$ can then be added to the other dynamical forces, $-\nabla E$, in the system.

I. Chemical Synthesis of Peptides

Potentially useful peptides within the scope of the present invention can be synthesized chemically by means well-known in the art such as, Merrifield solid phase peptide synthesis and its modem variants. For an exhaustive overview of chemical peptide synthesis, see Principles of Peptide Synthesis, M. Bodansky, Springer, Verlag (1984); Solid Phase Peptide Synthesis, J. M. Stewart and J. B. Young, 2d ed., Pierce Chemical Co. (1984); The Peptides: Analysis, Synthesis, and Biology, (pp. 3–285) G. Barany and R. B. Merrifield, Academic Press (1980). Each of these references is herein incorporated by reference for all purposes. In the solid-phase method, the synthesis starts at the carboxyl-terminal end of the peptide by attaching an alpha-amino protected amino acid such as, t-butyloxycarbonyl (Boc) or fluorenylmethyloxycarbonyl (Fmoc) protective groups, to a solid support. Suitable polystyrene resins consist of insoluble copolymers of styrene with about 0.5 to 2% of a cross-linking agent, such as divinyl benzene. These and other methods of peptide synthesis are also exemplified by U.S. Pat. Nos. 3,862,925, 3,842,067, 3,972,859, and 4,105,602.

The synthesis uses manual synthesis techniques, as in traditional Merrifield synthesis, or automatically employs peptide synthesizers. Both manual and automatic techniques are well known in the art of peptide chemistry. The resulting peptides can be cleaved from the support resins using standard techniques, such as HF (hydrofluoric acid) deprotection protocols as described in Lu, G. S., Int. J Peptide & Protein Res (1987) vol 29, pg. 545. Other cleavage methods include the use of hydrazine or TFA (tri-fluoracetic acid).

J. Recombinant Production of Peptides

As an alternative to chemical synthesis, the peptides designed by the methods described in the present disclosure can be produced by expression of recombinant DNA constructs prepared according to well-known methods. Such production can be desirable when large quantities are needed or when many different mutating peptides are required. Since the DNA of the wild type (or other related) peptide has often been isolated, mutation into modified peptide is possible.

The DNA encoding the mutated peptides is preferably prepared using commercially available nucleic acid synthesis methods. See Gait et at. "Oligonucleotide Synthesis; A Practical Approach" M. J. Gait, Ed., IRL Press, Oxford, England (1985) for a current overview of nucleic acid synthesis methods. Methods to construct expression systems for production in either natural or recombinant hosts are generally known in the art.

Expression can be affected in either prokaryotic or eucaryotic hosts. Prokaryotes most frequently are represented by various strains of *E. Coli*. However, other microbial strains may also be used, such as bacilli, for example *Bacillus subtilis*, species of pseudomonas, or other bacterial strains. In such procaryotic hosts, plasmid vectors that contain replication sites and control sequences derived from a species compatible with the host are used. For example, a common vector for *E. coli* is pBR322 and its derivatives. Commonly used procaryotic control sequences, which contain promoters for transcription initiation, optionally with an operator, along with ribosome binding-site sequences, include such commonly used promoters as the betalactamase and lactose (lac) promoter systems, the tryptophan (trp) promoter system, and the lambda-derived $P_L$ promoter. However, any available promoter system compatible with procaryotes can be used.

Expression systems useful in eucaryotic hosts consist of promoters derived from appropriate eucaryotic genes. A class of promoters useful in yeast, for example, includes promoters for synthesis of glycolytic enzymes, such as 3-phosphoglycerate kinase. Other yeast promoters include those from the enolase gene or the Leu2 gene obtained from YEp 13.

Suitable mammalian promoters include the early and late promoters from SV40 or other viral promoters such as those derived from polyoma, adenovirus II, bovine papilloma virus or avian sarcoma viruses. Suitable viral and mammalian enhancers are cited above. When plant cells are used as an expression system, the nopaline synthesis promoter, for example, is appropriate.

The expression systems are constructed using well-known restriction and ligation techniques and transformed into appropriate hosts. Transformation is done using standard techniques appropriate to such cells. The cells containing the expression systems are cultured under conditions appropriate for production.

It will be readily appreciated by those having ordinary skill in the art of peptide design that the peptides that are designed in accordance with the present disclosure and subsequently synthesized are themselves novel and useful compounds and are thus within the scope of the invention.

K. Testing New Peptides

After the peptides have been synthesized by either chemical or recombinant methods, the physical properties can be measured using a variety of physical techniques. For example, thermal stability can be determined by assaying a specific property of the mutated protein at different temperatures as is well known in the art. Physical stability is a structural property, and generally indicates the stability of a folded conformation of the peptide relative to an unfolded or denatured state. The peptide may also be tested in various assays to determine the avidity and specificity with which it bonds to certain ligands. Such assays as RIA, ELISA, etc. are generally suitable and are well-known in the art. Many methods such as spectroscopy, sedimentation analysis, chemical assays, etc. can determine whether a peptide has undergone a structure change. For example, NMR, circular dichroism, fluorescent transfer, etc. can measure the folded state of a peptide at different conditions.

V. Example

Polyalanine in chains of 5, 10, and 20 amino acids was simulated according to the constrained Langevin dynamics method described above. Polyalanine was chosen because it is known to form α-helixes. All the simulations were carried out with simple terminations of the peptides, i.e. no special termini were applied to the chain.

Figure 8:
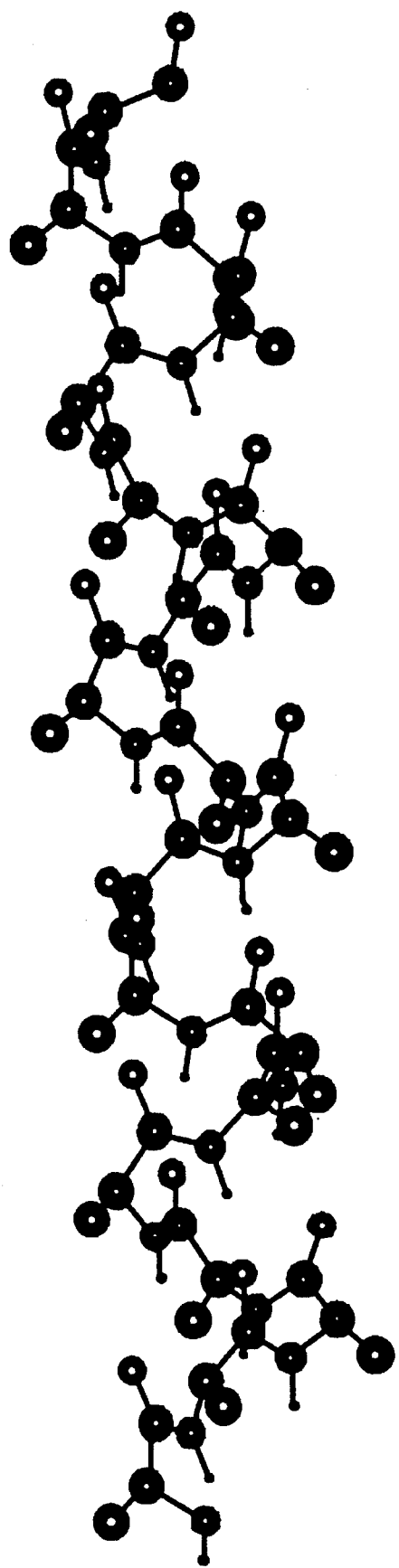
FIG. 8 is a molecular representation of an initial conformation of polyalanine used in an example performed in accordance with the present invention.
Figure 9A:
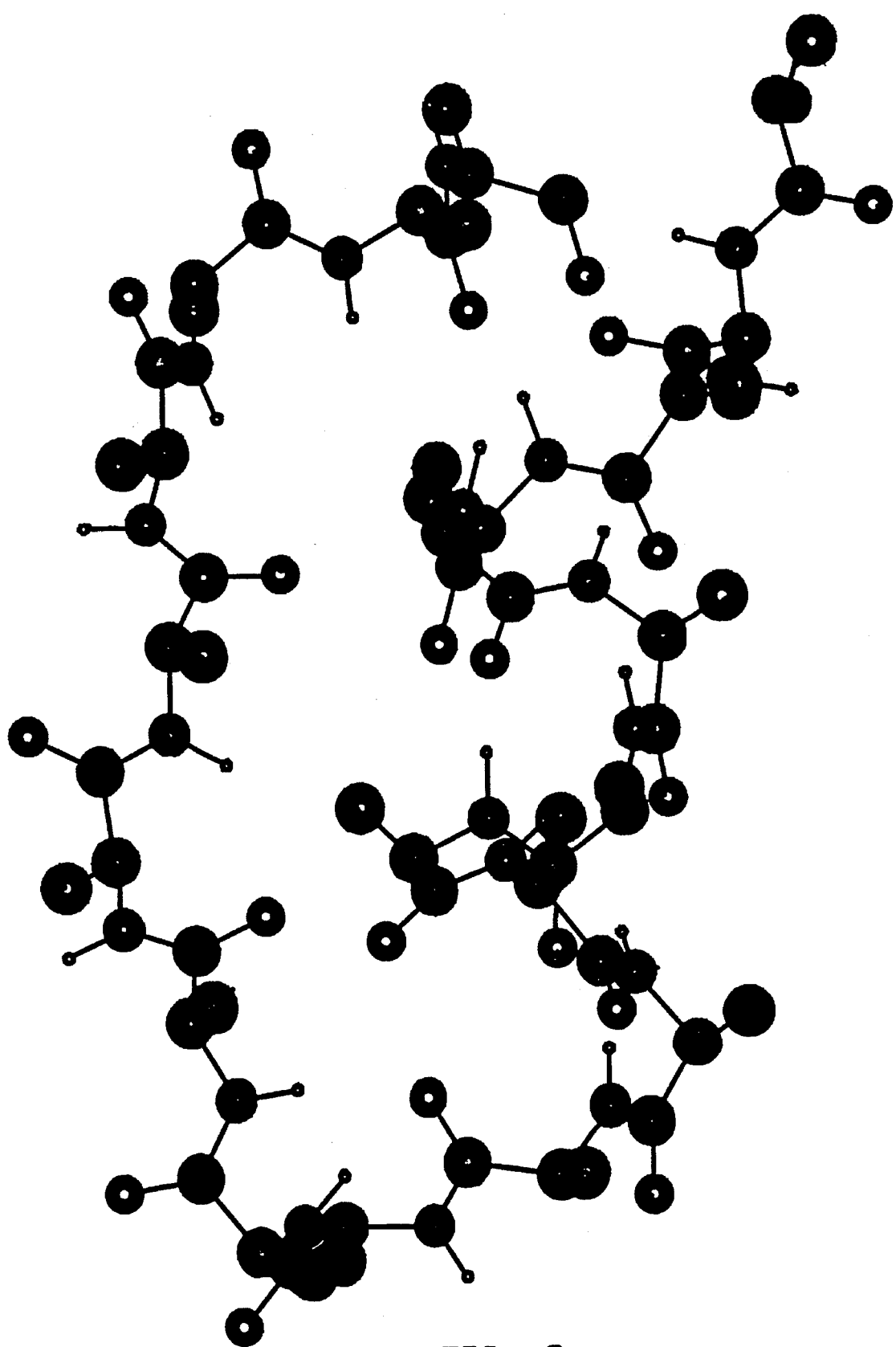
FIGS. 9a–d are molecular representations of polyalanine in various conformations as it evolves from the initial state shown in FIG. 8 according to a preferred simulation of the invention.
Figure 9B:
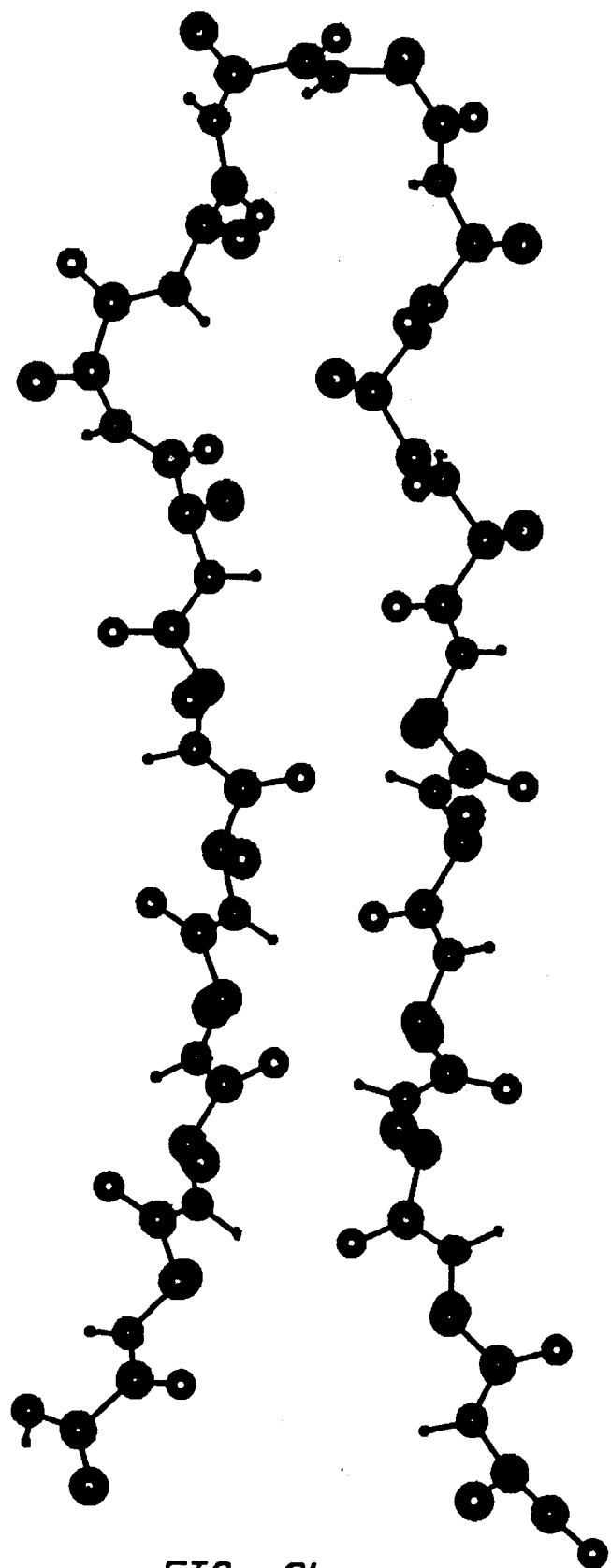
Figure 9C:
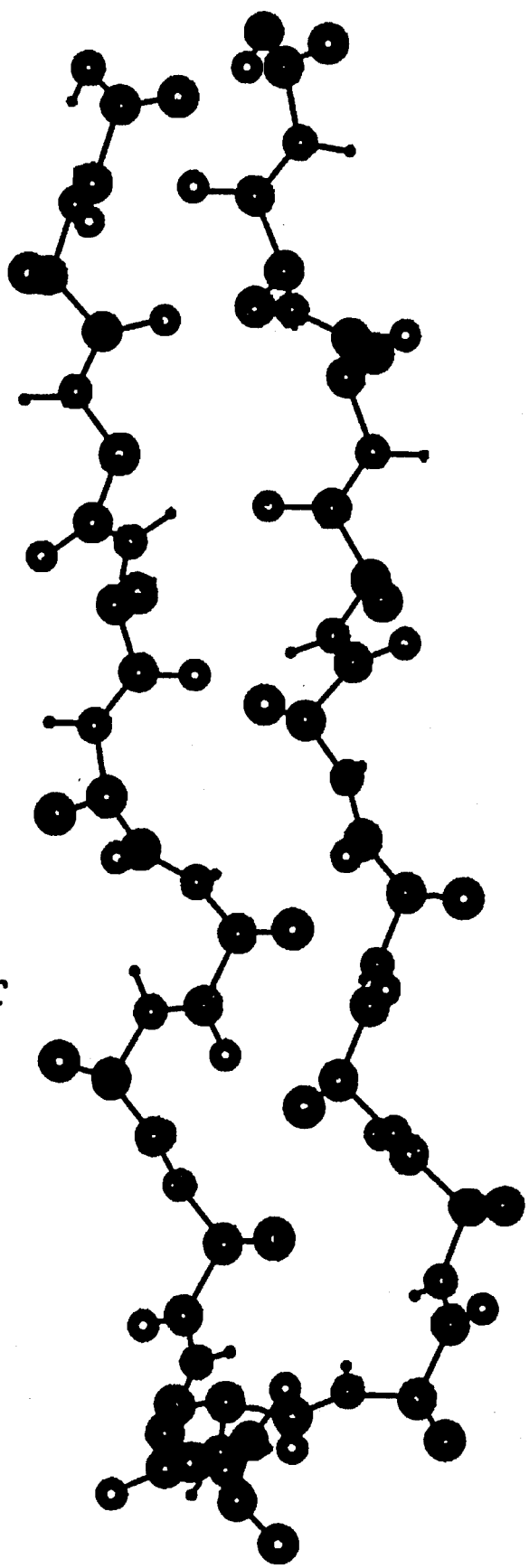
Figure 9D:
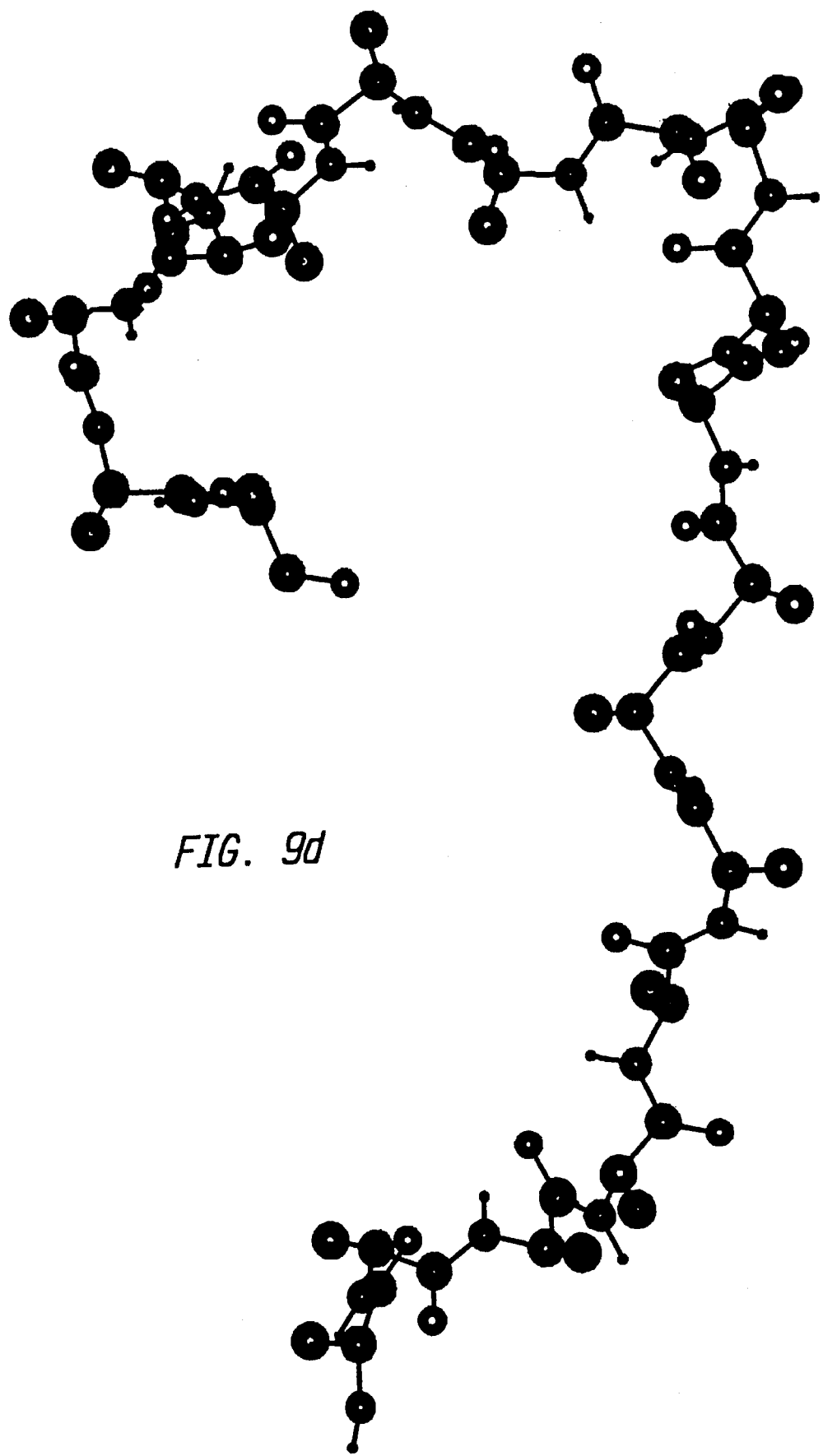
Figure 10A:
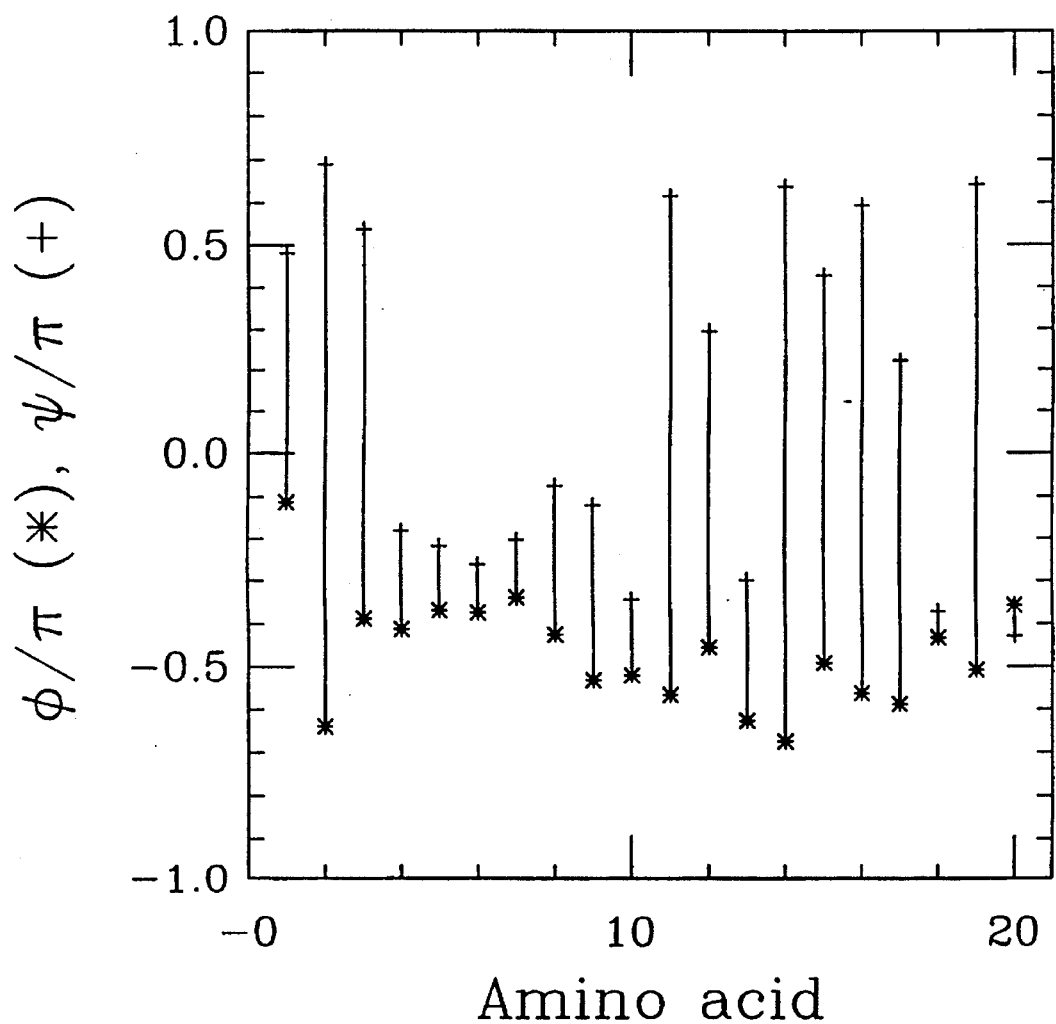
FIGS. 10a–d are graphs showing the numerical values of the $\phi$ and $\Psi$ angles in each of the conformations shown in FIGS. 9a–d.
Figure 10B:
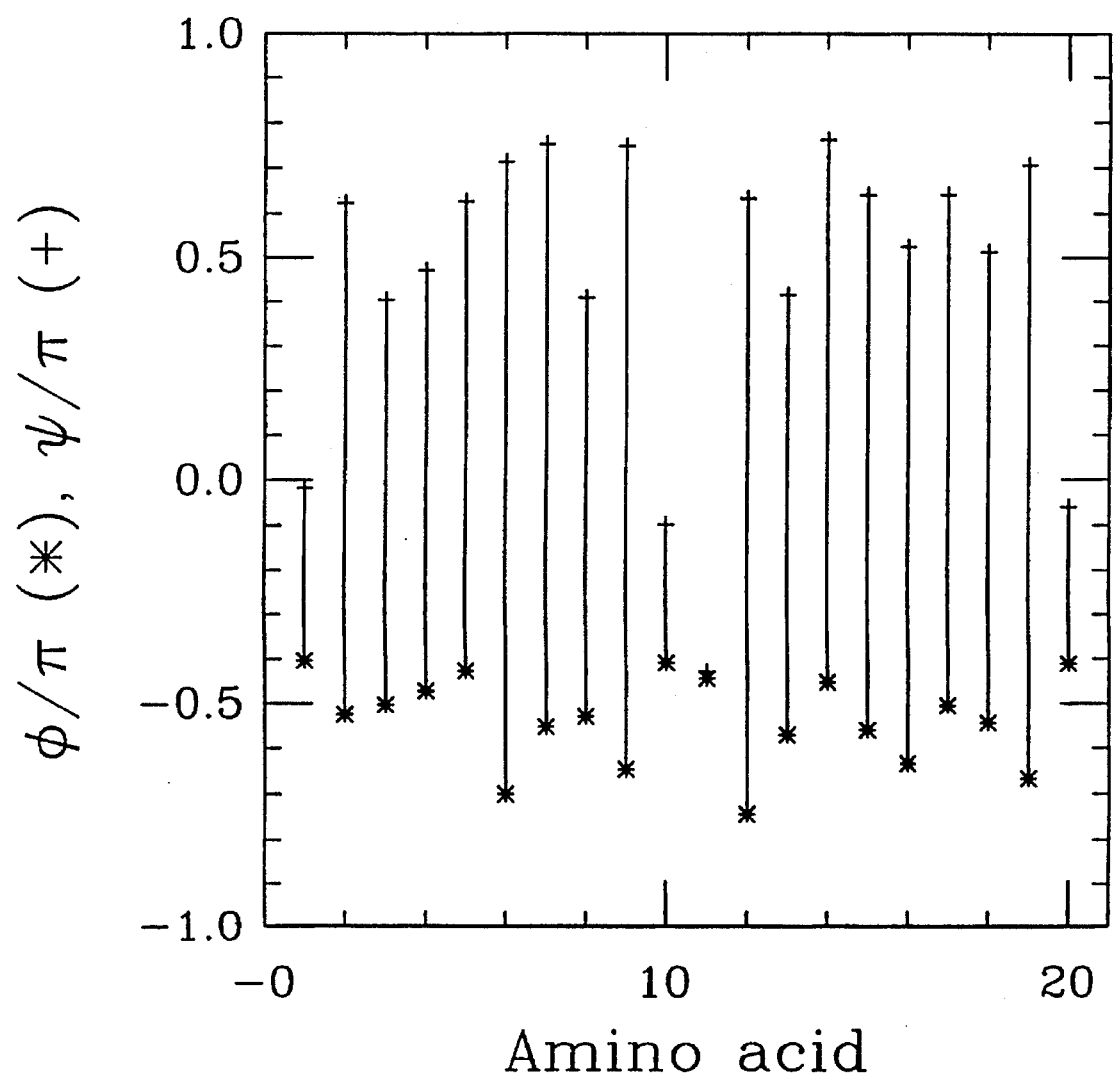
Figure 10C:
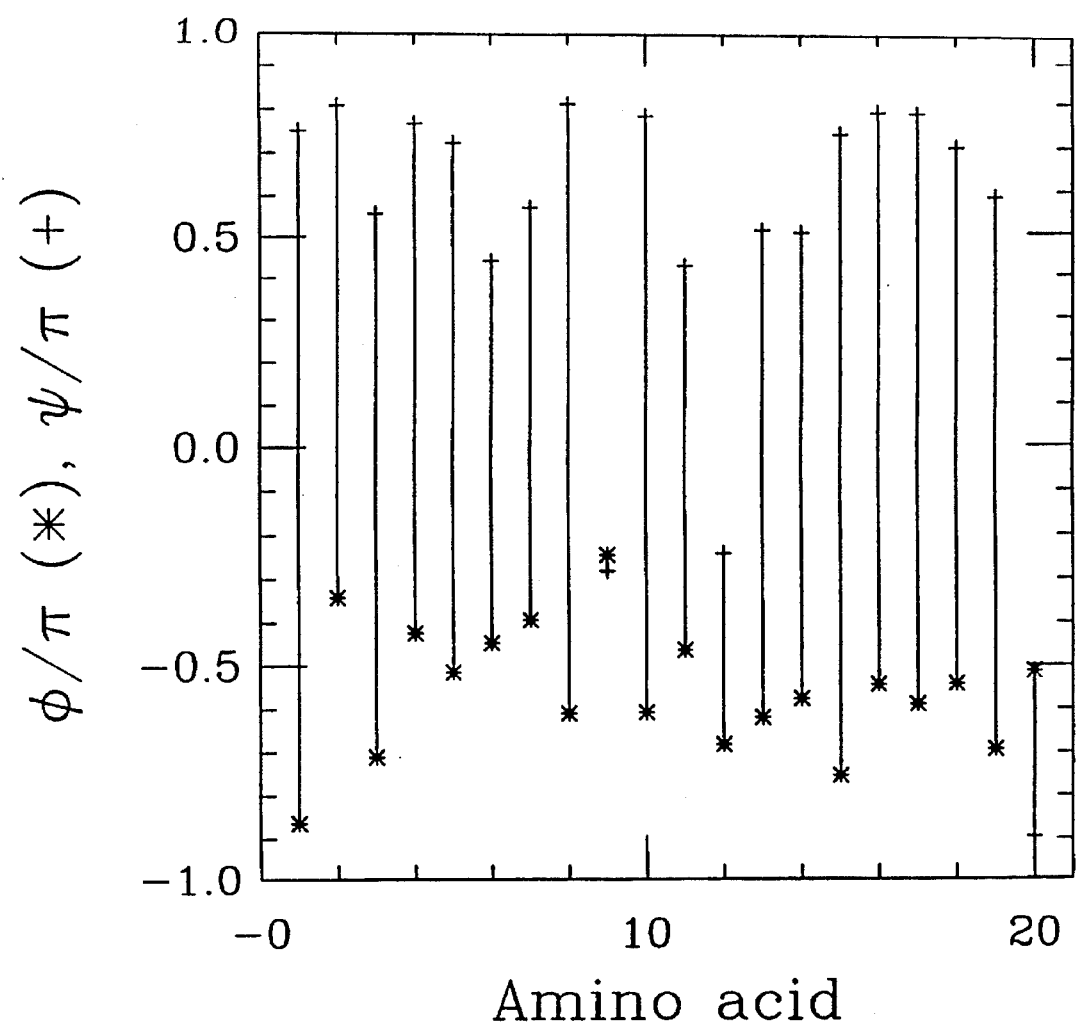
Figure 10D:
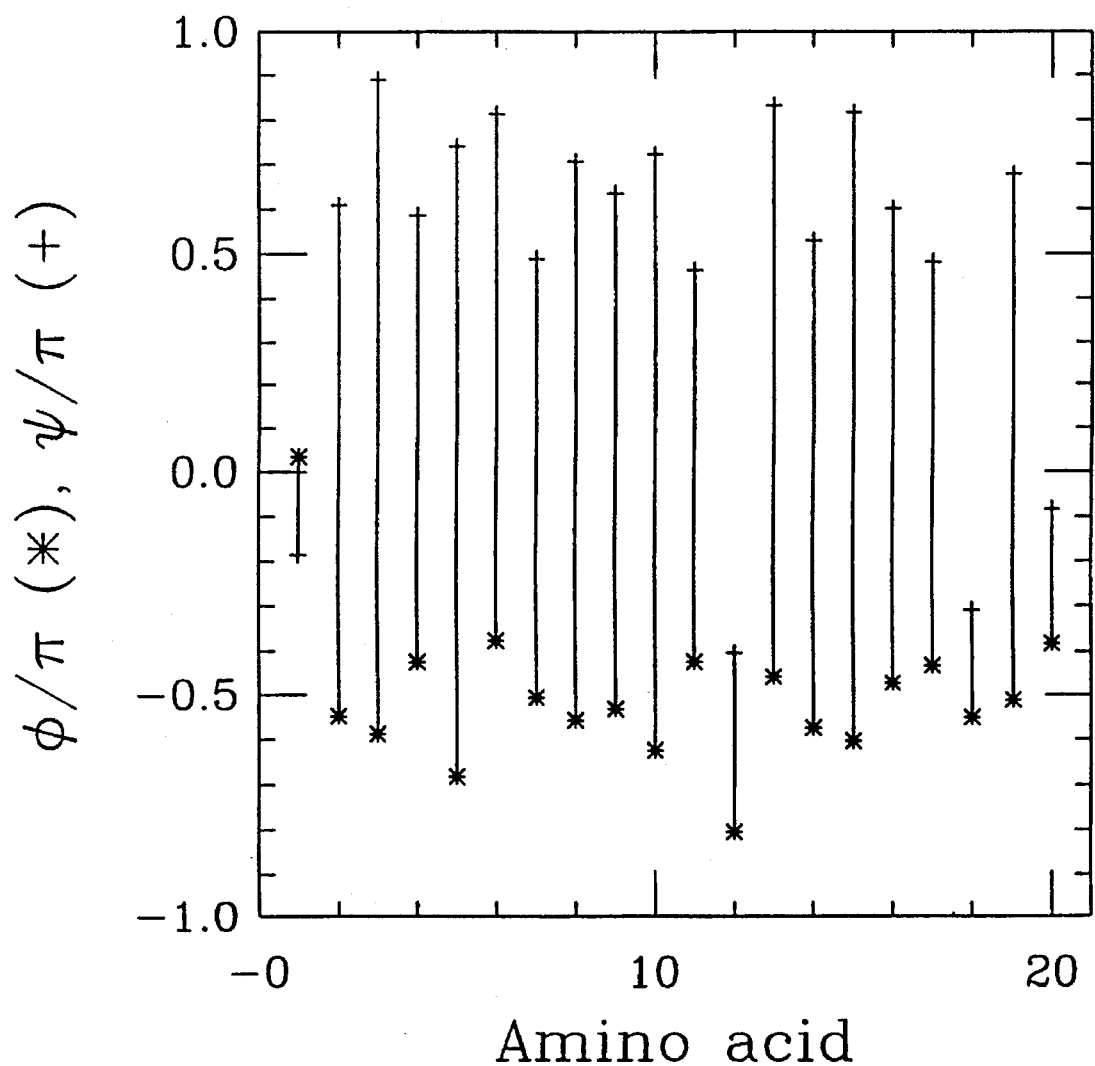

The constraints based upon the six amino acid subunits (described in the "Initial Conformation" section above) were applied with the beta-carbon representing the entire alanine side chain ($CH_3$). The initial condition for the simulations was an α-helix conformation, relaxed at T=0. This conformation is shown in FIG. 8 for $N_a$=20. The simulations neglected all hydrodynamic effects in the system, i.e. the friction matrix $\Xi$ was taken to be diagonal and there were no explicit water molecules in the system. Neglecting the hydrodynamic correlations in the friction simplifies the evaluation of the constraint forces considerably. Because $\Xi$ is diagonal, the $s_{ij}$ can be found as a solution to a banded matrix equation. All atoms in the representation were assumed to have the same effective radius in interaction with the solvent, $a_i$=3Å. The effect of the solvent is then implemented through the characteristic friction $\xi_0 = 6\pi\zeta a_u$. Using the viscosity of water, $\xi$=0.9 cp we then obtain the characteristic time, $$\tau = \xi_0 r_0^2 / E_0 \approx 75 ps \qquad (14)$$

In using this characteristic time, it is implied that $\xi_{ii}=v_{ii}=1$, since all atoms are assumed to have the same friction.

The dynamical interactions were modeled as described in Eqs. (3)–(6) with n=18, m=3, and $r_c$=10. The parameters $A_i$, $B_i$, and $q_i$ were taken form Jorgensen, et al., *Journal or the American Chemical Society*, 110:1657–1666 (1988), previously incorporated by reference. Effects of dielectric screening were included through the phenomenological dielectric function $\epsilon(r)=\exp(r/3)$ as shown in Eqs. 3 and 4.

Several tests of $1-2\cdot10^6$ time steps each (about 24 hours on a Silicon Graphics Inc, workstation were ran starting from the helical conformations. Each time, a given temperature for 100 normalized time units was then applied before averaging the energy over the next 100 normalized time units (7.5 ns). After this initial period, the helix starts to unfold, and the system moves away from its initial helical region of phase space. The system was observed to remain in metastable conformations for relatively long times (on the order of fractions of a μ-sec).

The unfolding process can take several forms depending on the temperature and the stochastic behavior of the problem. Typically, the behavior falls into two groups: direct unfolding and unfolding through intermediate folded states. Studying 50 different unfolding trajectories, each having the α-helix conformation as initial condition, a kinetic pathway for each of the two groups was identified. For the first, the unfolding through the intermediate metastable state, the chain of 20 amino acids starts to unfold from the C-terminus; for the second, direct unfolding, the chain unfolds from the N-terminus. Two examples of the unfolding process at high temperatures are shown in FIGS. 9–12—one example for each of the above cases.

In FIGS. 9 and 10, a few snapshots of the structure at different times in the simulation are shown. FIGS. 9a and 10a show the partly unfolded state—unfolding from the C-terminus. Note that the structure seems to maintain its α-helix conformation away from the unfolded C-terminus. In FIGS. 9a and 10a, the structure has approximately two complete helix turns intact. This is connected to the fact that the unfolded part of the chain (essentially a β-sheet state) slides along the α-helix part of the conformation. This way, the unfolded part of the chain can maintain the unfolding process localized to the turning point between the remaining α-helix and unfolded state. A direct consequence of this behavior is that the conformation slides in to a perfect β-sheet conformation, as seen in FIGS. 9b and 10b. This state is stable over a very long time depending on the applied temperature. For reduced T=1.5, the β-sheet was observed to be present for several microseconds before unfolding to a conformation with no hydrogen bonds. For the higher temperature (T=$2T_0$), a long lived β-sheet with one or two turns over several hundred nanoseconds (see FIGS. 9b, 10b, 9c, and 10c) was typically observed. Eventually, even the β-sheet breaks due to the high temperature. Such an unfolded state is shown in FIGS. 9d and 10d. Similar metastable β-sheet states have also been seen by others in monte-carlo generated ensembles for poly-alanine.

Figure 11A:
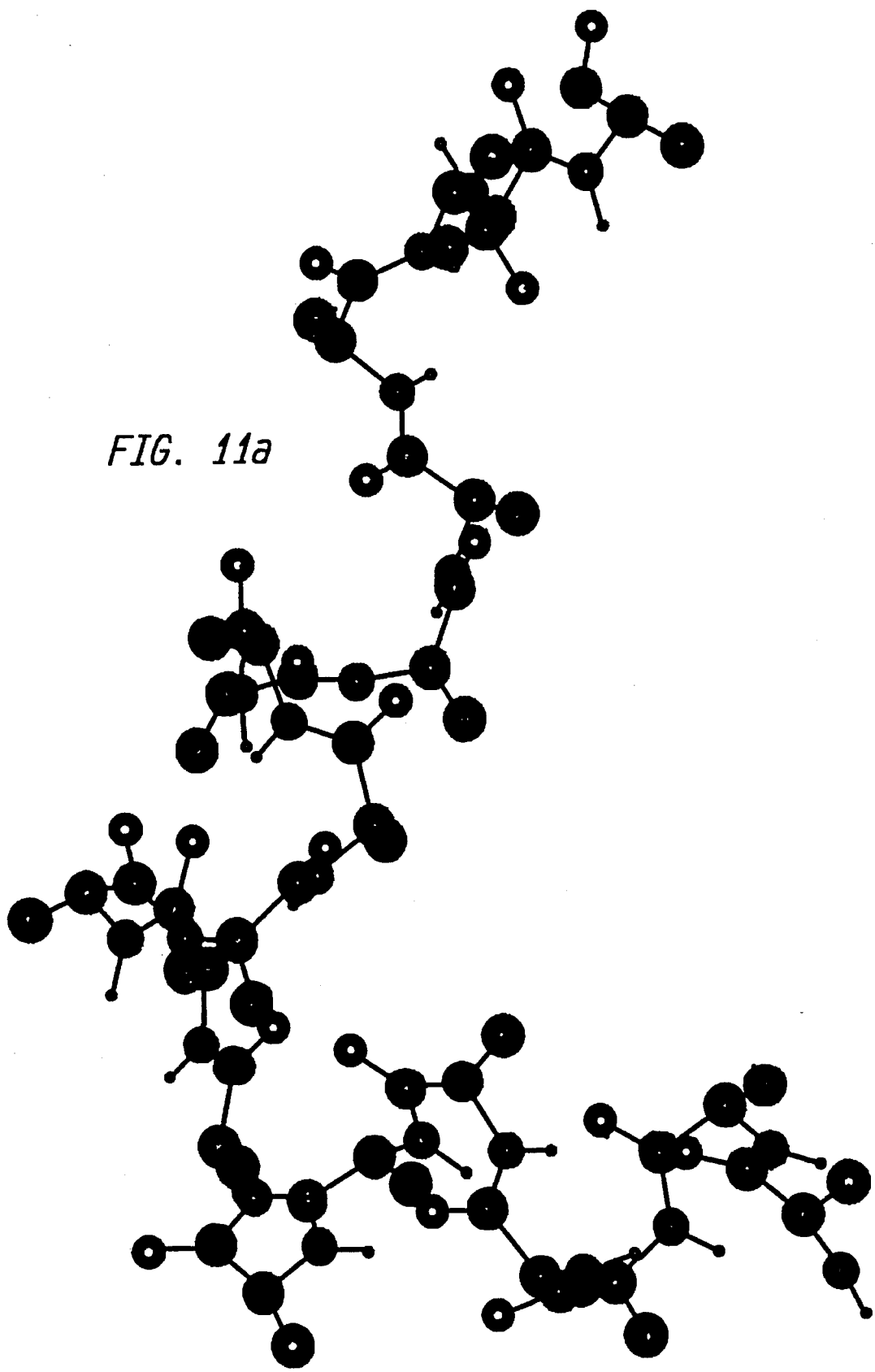
FIGS. 11a–c are molecular representations of polyalanine in various conformations as it evolves in a different example.
Figure 11B:
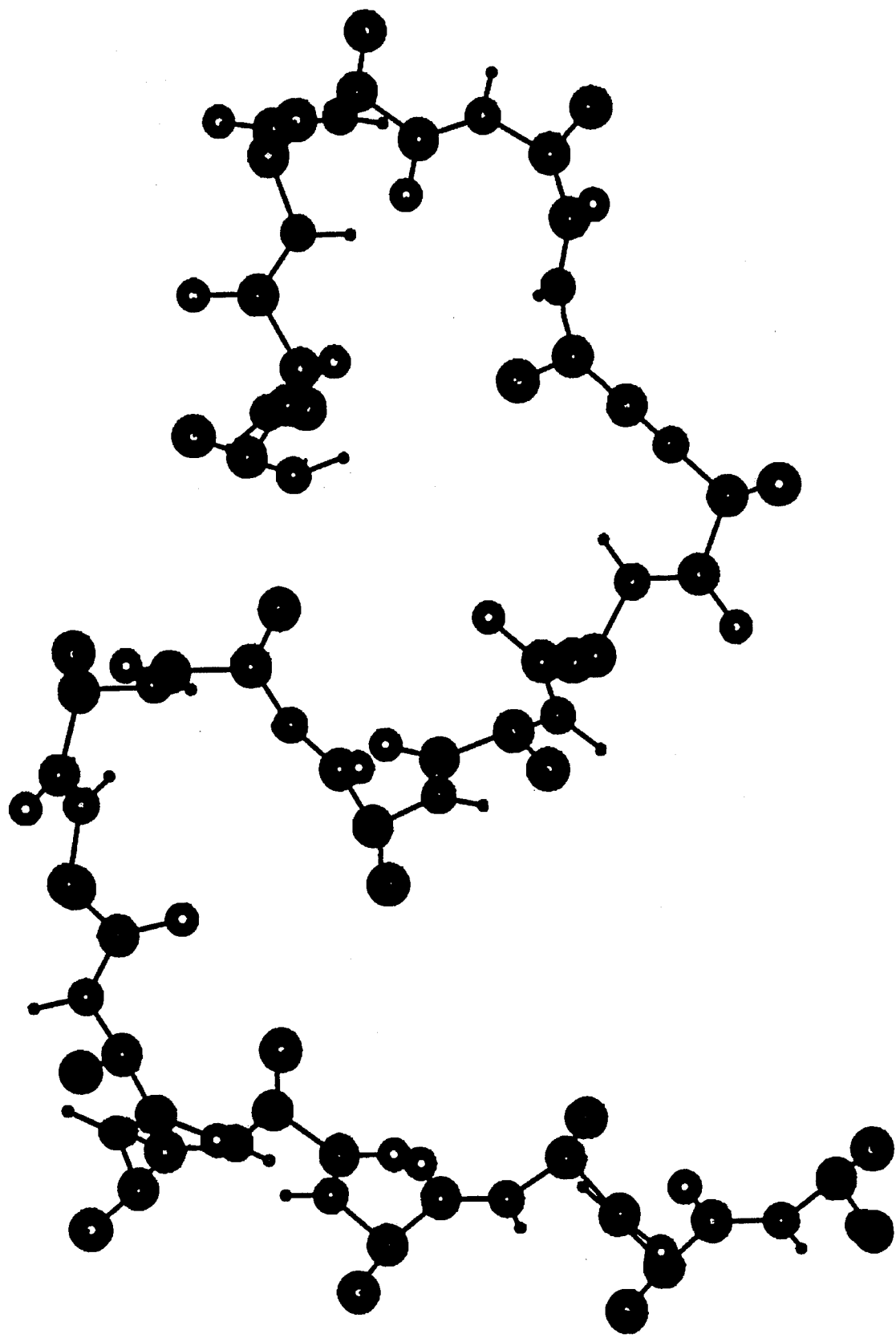
Figure 11C:
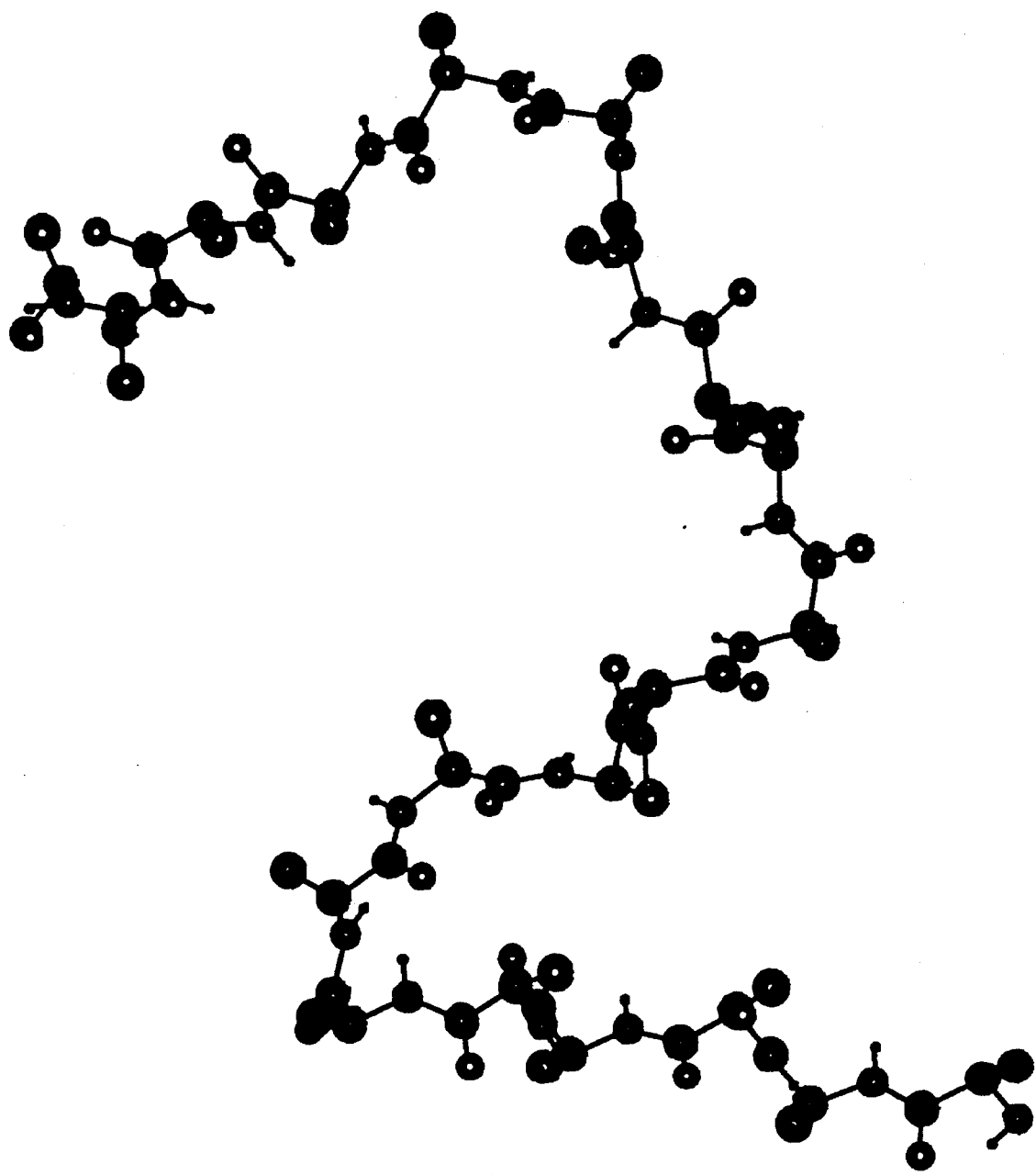
Figure 12A:
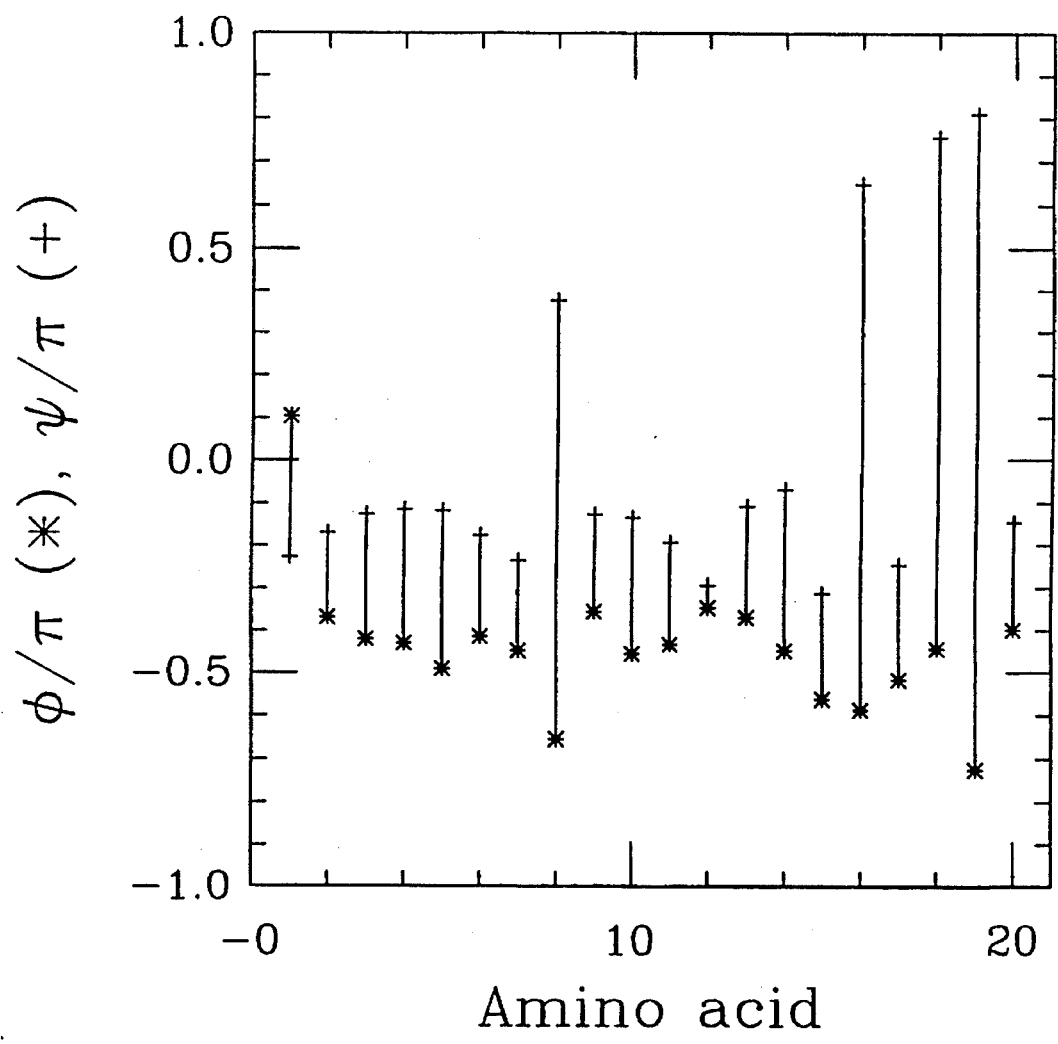
FIGS. 12a–c are graphs showing the numerical values of the $\phi$ and $\Psi$ angles in each of the conformations shown in FIGS. 11a–c.
Figure 12B:
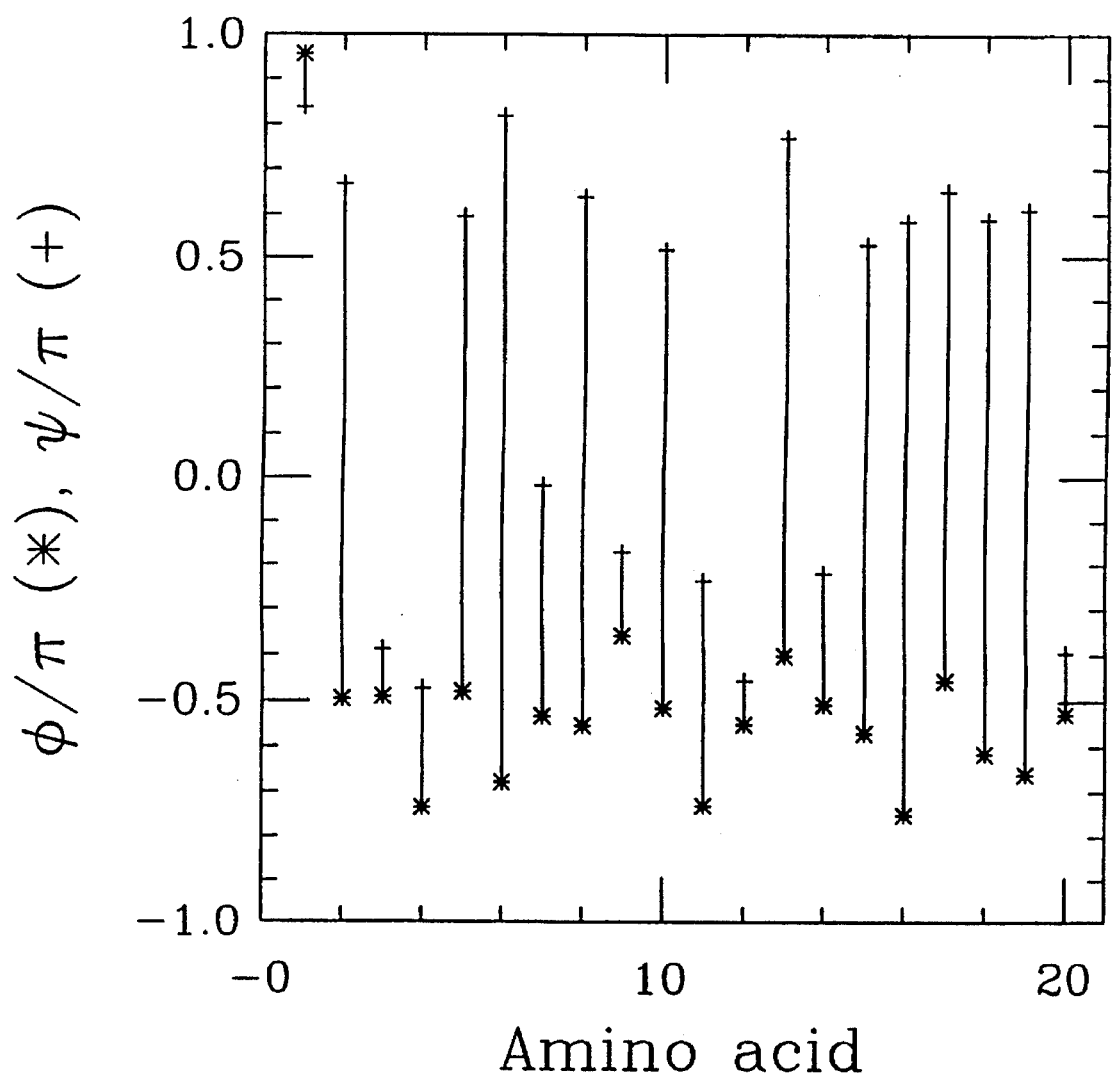
Figure 12C:
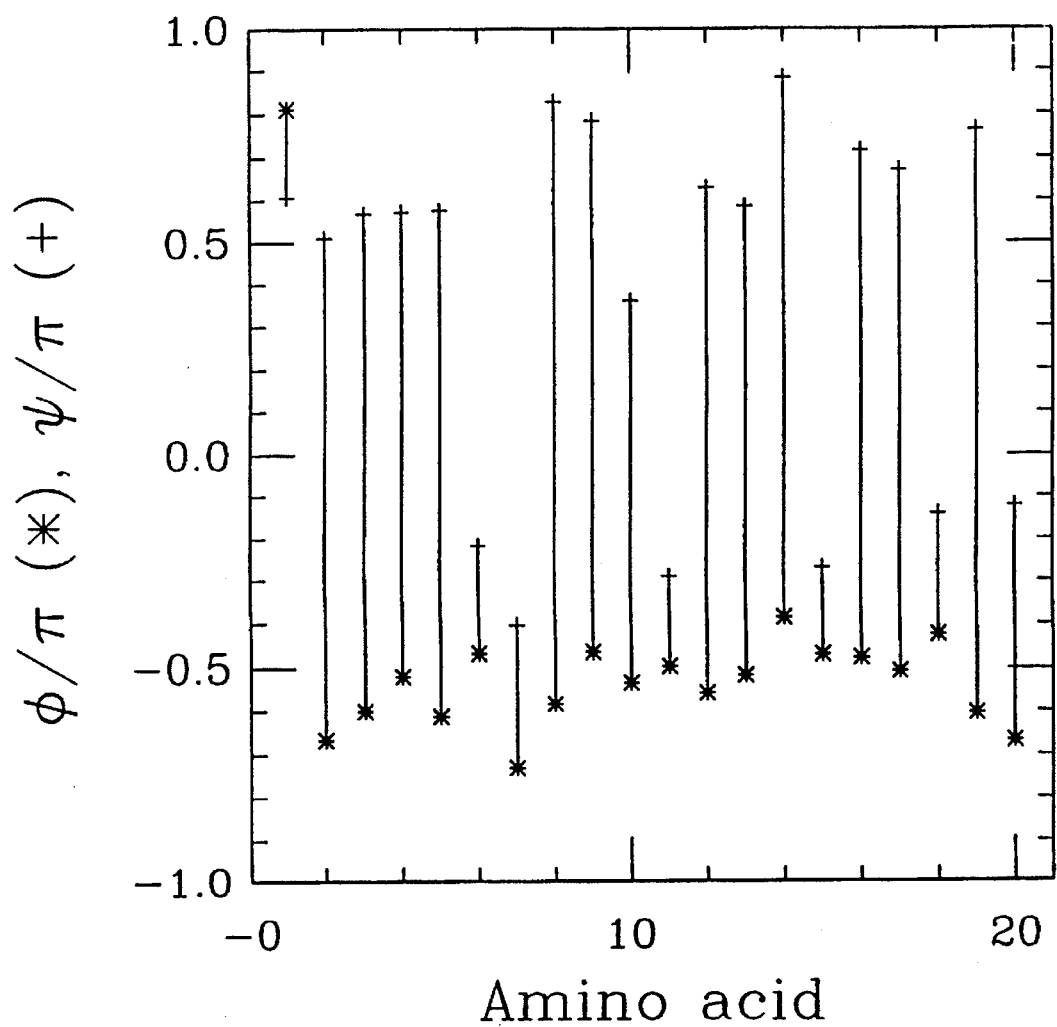
Figure 13:
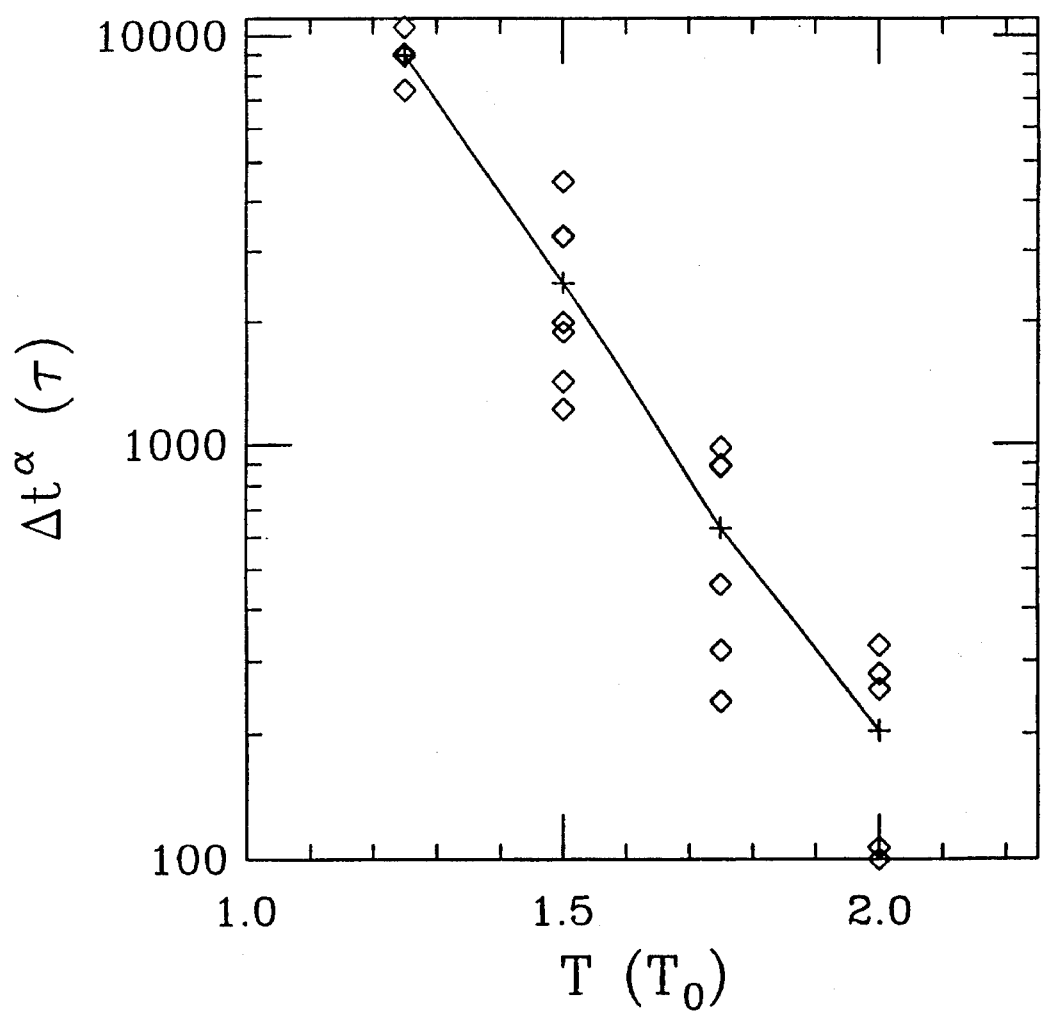
FIG. 13 is a graph illustrating the effect of hydrogen bonding in a simulation employing a potential function including the effect of dielectric screening.

The other type of unfolding is shown in FIGS. 11 and 12. Again, the initial conformation was the α-helix structure shown in FIG. 8. The thermal noise does, however, this time result in unfolding from the other terminus as well. Due to the geometry of the bond angles in the system, unfolding from the N-terminus does not give rise to contact between the unfolded and the remaining α-helix amino acids. This is shown in FIGS. 11 a–c, where the chain obviously uncurls without any intermediate states. As a result of this simpler unfolding process, the unfolding time was observed to be much shorter than when the chain unfolds from the C terminus. Because the helix unfolding times appear to be much longer than the ~500 picosec found for molecular dynamics simulations of an α-helix unfolding in water, it appears that the screened OPLS potentials may not have been sufficient in themselves for simulating the hydrogen-bond interactions when solvent is not explicitly represented. To test this, a variety of temperatures were ran and plotted as unfolding time vs. T in FIG. 13. As may be seen, the potentials need to be renormalized by a factor of 3 or so to approximate the solvated behavior. Of course, as noted above, when a rapid exploration of conformation space is desired, the contribution of the solvent (including contribution of hydrogen bonding) need not be quantitatively accurate.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of simulating the conformations of a molecular system with the aid of a computer system, the molecular system having a plurality of atoms partially limited in their ability to move with respect to one another by constraining forces and frictional forces, the method comprising the following steps:
   (a) inputting into the computer system a computer usable representation of the molecular system, the representation having an arrangement of atoms determined, in part, by the constraining forces, the representation also having degrees of freedom;
   (b) determining the interatomic non-bonding forces acting on each atom of the representation, the interatomic non-bonding forces acting on each atom caused by the other atoms in the molecular system;
   (c) obtaining a total non-frictional force on the atoms by
      (i) combining thermal noise forces with the interatomic non-bonding forces acting on each atom, and
      (ii) projecting out of said interatomic non-bonding forces and noise forces, those force components in the directions of the constraining forces in the molecular system such that the atoms of the representation are constrained to their positions with respect to other atoms in the direction of the constraining forces; and
   (d) moving the atoms of the representation into a new conformation as determined by an overdamped Langevin dynamics description of the forces acting on the atoms, the overdamped Langevin description including the total nonfrictional forces and the frictional forces, wherein movement of the atoms is used to determine one or more specified properties of the molecular system.

2. The method of claim 1 wherein the step of inputting into the computer system a computer usable representation of the molecular system includes a step of determined the constraining forces in the representation of the molecular system from the equilibrium lengths and angles of one or more chemical bonds in the molecular system.

3. The method of claim 1 wherein the molecular system is a biological macromolecule.

4. The method of claim 3 wherein the biological macromolecule is a peptide or protein.

5. The method of claim 4 wherein the step of inputting into the computer system a computer usable representation of the molecular system includes a step of selecting the representation's degrees of freedom from the group consisting of $\phi$ bonds angles of amino acids in the peptide or protein, $\Psi$ bond angles of amino acids in the peptide or protein, $\omega$ bond angles between adjacent amino acids in the peptide or protein, $\chi$ bond angles of amino acids in the peptide or protein, and combinations of these bond angles.

6. The method of claim 1 wherein the step of determining the interatomic non-bonding forces acting on each atom of the representation includes a step of approximating the electrostatic and steric forces between the atom under consideration and other atoms in the molecular system.

7. The method of claim 6 wherein the step of approximating the electrostatic and steric forces considers only those steric and electrostatic forces existing between the atom under consideration and those other atoms in the molecular system within a fixed cut-off distance from the atom under consideration.

8. The method of claim 1 wherein the step of moving the atoms of the representation includes moving the atoms over a specified time step of less than about 10 picoseconds.

9. The method of claim 8 wherein the time step is between about 0.5 and 10 picoseconds.

10. The method of claim 1 further comprising a step of repeating steps b through d until a predefined event occurs.

11. The method of claim 10 wherein the predetermined predefined event is repeating steps b through d a specified number of times, 12. The method of claim 1 wherein the step of moving the atoms of the representation into new conformations as determined by an overdamped Langevin dynamics description of the forces acting on the atoms employs a first order expression of the Langevin dynamics description.

13. The method of claim 12 wherein the step of moving the atoms of the representation to new locations according to the total non-frictional forces and said frictional forces includes a step of determining the motion of the atoms according to the following vector expression:

$$\Xi \dot{R} = -\nabla E + N + S \Rightarrow$$

$$\dot{R} = \Xi^{-1}\{-\nabla E + NS\}$$

where R is a position vector, $\Xi$ is a friction matrix acting on the individual atoms of the representation, N is a Langevin thermal noise force vector, $\Xi^{-1}$ is the inverse of the friction matrix $\Xi$, and S is a constraining force vector.

14. The method of claim 1 wherein the noise forces used in the step of combining thermal noise forces with the interatomic non-bonding forces are uncorrelated from atom to atom in the representation of the molecular system.

15. The method of claim 1 wherein the noise forces used in the step of combining thermal noise forces with the interatomic non-bonding forces are described by a gaussian distribution.

16. The method of claim 1 wherein the step of projecting out of said interatomic non-bonding forces and noise forces is accomplished by means of a matrix inversion of a set of simultaneous equations.

17. A method for producing a peptide or protein having a desired conformation, one or more degrees of freedom, and a plurality of possible conformations, the peptide or protein also having a plurality of atoms partially limited in their ability to move with respect to one another by constraining forces and frictional forces, the method comprising the following steps:
   (a) inputting into the computer system a computer usable representation of the peptide or protein, the representation having an arrangement of atoms determined, in pan, by the constraining forces, the representation also having degrees of freedom;
   (b) determining the interatomic non-bonding forces acting on each atom of the representation, the interatomic non-bonding forces acting on each atom caused by the other atoms in the molecular system;
   (c) obtaining a total non-frictional force on the atoms by
      (i) combining thermal noise forces with the interatomic non-bonding forces acting on each atom, and
      (ii) projecting out of said interatomic non-bonding forces and noise forces, those force components in the directions of the constraining forces in the molecular system such that the atoms of the representation are constrained to their positions with respect to other atoms in the direction of the constraining forces;
   (d) moving the atoms of the representation into a new conformation as determined by an overdamped Langevin dynamics description of the forces acting on the atoms, the overdamped Langevin description including the total non-frictional forces and the frictional forces;

(e) repeating steps b through d until it can be determined whether the peptide or protein has the desired conformation; and (f) preparing the peptide or protein if it has the desired conformation.

18. The method of claim 17 wherein the step of repeating steps b through d until it can be determined whether the peptide or protein has the desired conformation includes a step of determining whether the peptide or protein has a conformation suitable for binding to a defined ligand.

19. The method of claim 17 wherein the step of repeating steps b through d until it can be determined whether the peptide or protein has the desired conformation includes a step of determining whether the peptide or protein has a conformation suitable for accepting a peptide segment having a defined primary sequence.

20. The method of claim 17 wherein the step of preparing the peptide or protein involves preparing the peptide or protein by chemical synthesis.

21. The method of claim 17 wherein the step of preparing the peptide or protein involves preparing the peptide or protein by expressing recombinant nucleic acids.

22. A method of simulating the conformations of a peptide with the aid of a computer system, the peptide having a plurality of atoms partially limited in their ability to move with respect to one another by constraining forces and frictional forces, the method comprising the following steps:

(a) inputting into the computer system a computer usable representation of the peptide, the representation having an arrangement of atoms determined, in part, by the constraining forces, the representation also having degrees of freedom;

(b) determining the interatomic non-bonding forces acting on each atom of the representation, the interatomic non-bonding forces acting on each atom caused by the other atoms in the molecular system;

(c) obtaining a total non-frictional force on the atoms by
  (i) combining thermal noise forces with the interatomic non-bonding forces acting on each atom, and
  (ii) projecting out of said interatomic non-bonding forces and noise forces, those force components in the directions of the constraining forces in the molecular system such that the atoms of the representation axe constrained to their positions with respect to other atoms in the direction of the constraining forces; and (d) moving the atoms of the representation into a new conformation as determined by an overdamped Langevin dynamics description of the forces acting on the atoms, the overdamped Langevin description including the total non-frictional forces and the frictional forces wherein movement of the atoms is used to determine one or more specified properties of the peptide.

23. The method of claim 22 wherein the step of inputting into the computer system a computer usable representation of the peptide includes a step of introducing atoms making up peptide bonds and introducing dummy atoms which exert forces only on the atoms forming at least some of the peptide bonds, the dummy atoms being arranged with respect to the atoms of the peptide bonds such that the peptide bonds are maintained in a planar conformation during the step of moving the atoms of the representation into a new conformation.

24. The method of claim 22 wherein the step of inputting into the computer system a computer usable representation of the peptide includes a step of selecting the representation's degrees of freedom from the group consisting of $\phi$ bonds angles of amino acids in the peptide or protein, $\Psi$ bond angles of amino acids in the peptide or protein, $\Psi$ bond angles between adjacent amino acids in the peptide or protein, $\chi$ bond angles of amino acids in the peptide or protein, and combinations of these bond angles.

25. The method of claim 22 wherein the step of inputting into the computer system a computer usable representation of the peptide includes a step of determining the constraining forces in the representation of the peptide from the equilibrium lengths and angles of one or more chemical bonds in the peptide.

26. The method of claim 22 wherein the step of determining the interatomic non-bonding forces acting on each atom of the representation includes a step of approximating the electrostatic and steric potentials between the atom under consideration and other atoms in the molecular system according to the following expression:

$$\tilde{E}_{ij}(r_{ij}) = \frac{q_i q_j}{\epsilon(r_{ij}) r_{ij}} + \frac{\sqrt{A_i A_j}}{r_{ij}^{12}} - \frac{\sqrt{B_i B_j}}{r_{ij}^6}$$

where q is the partial charge on an atom, A and B are steric interaction parameters, r is the distance between the atom under consideration and another atom, $\epsilon(r)$ is a dielectric screening function, and E is a combined electrostatic and steric potential.

27. The method of claim 22 further comprising a step of repeating steps b through d until a predefined event occurs, each step of repeating taking place over a specified time step.

28. The method of claim 27 wherein the specified time step is between about 0.5 and 10 picoseconds.

29. A computer readable medium storing instructions for simulating the conformations of a molecular system having a plurality of atoms partially limited in there ability to move with respect to one another by constraining forces an frictional forces, the medium comprising instructions for performing the following steps:

(a) inputting into a computer system a computer usable representation of the molecular system, the representation having an arrangement of atoms determined, in part, by the constraining forces, the representation also having degrees of freedom;

(b) determining the interatomic non-bonding forces acting on each atom of the representation the interatomic non-bonding forces acting on each atom caused by the other atoms in the molecular system;

(c) obtaining a total non-frictional force on the atoms by
  (i) combining thermal noise forces with the interatomic non-bonding forces acting on each atom, and
  (ii) projecting out of said interatomic non-bonding forces and noise forces, those force components in the directions of the constraining forces in the molecular system such that the atoms of the representation are constrained to their positions with respect to other atoms in the direction of the constraining forces; and (d) moving the atoms of the representation into a new conformation as determined by an overdamped Langevin dynamics description of the forces acting on the atoms, the overdamped Langevin description including the total non-frictional forces and the frictional forces, wherein movement of the atoms is used to determine one or more specified properties of the molecular system.

30. The computer readable medium of claim 29 wherein the instructions for the step of imputting into the computer sysetm a computer usable representation of the molecular system include instructions for a step of determining the constraining forces in the representation of the molecular system form the equilibrium lengths and angels of one or more chemical bonds in the molecular system.

31. The computer readable medium of claim 29 wherein the molecular system is a biological macromolecule.

32. The computer readable medium of claim 31 wherein the biological macromolecule is a peptide or protein.

33. The computer readable medium of claim 32 wherein the instructions for the step of inputting into the computer system a computer usable representation of the molecular system include instructions for a step of selecting the representation's degrees of freedom from the group consisting of f bonds angles of amino acids in the peptide or protein, y bond angles of amino acids in the peptide or protein, w bond angles between adjacent amino acids in the peptide or protein, c bond angles of amino acids in the peptide or protein, and combinations of these bond angles.

34. The computer readable medium of claim 29 wherein the instructions for the step of determining the interatomic non-bonding forces acting on each atom of the representation include instructions for a step of approximating the electrostatic and steric forces between the atom under consideration and other atoms in the molecular system.

35. The computer readable medium claim 34 wherein the instructions for step of approximating the electrostatic and steric forces require consideration of only those steric and electrostatic forces existing between the atom under consideration and those other atoms in the molecular system within a fixed cut-off distance from the atom under consideration.

36. The computer readable medium of claim 29 wherein the instructions for the step of moving the atoms of the representation include instructions for moving the atoms over a specified time step of less than about 10 picoseconds.

37. The computer readable medium of claim 36 wherein the time step is between about 0.5 and 10 picoseconds.

38. The computer readable medium of claim 29 further comprising instructions for a step of repeating steps b through d until a predefined event occurs.

39. The computer readable medium of claim 38 wherein the predetermined predefined event is repeating steps b through d a specified number of times.

40. The computer readable medium of claim 29 wherein the instructions for the step of moving the atoms of the representation into new conformations as determined by an overdamped Langevin dynamics description of the forces acting on the atoms include instructions for employing a first order expression of the Langevin dynamics description.

41. The computer readable medium of claim 40 wherein the instructions for the step of moving the atoms of the representation to new locations according to the total non-frictional forces and said frictional forces include instructions for a step of determining the motion of the atoms according to the following vector expression:

$$\Xi \dot{R} = -\nabla E + N + S \Rightarrow \dot{R} = \Xi^{-1}\{-\nabla E + NS\}$$

where R is a position vector, X is a friction matrix acting on the individual atoms of the representation, N is a Langevin thermal noise force vector, $X^{-1}$ is the inverse of the friction matrix X, and S is a constraining force vector.

42. The computer readable medium of claim 29 wherein the noise forces used in the step of combining thermal noise forces with the interatomic non-bonding forces are uncorrelated from atom to atom in the representation of the molecular system.

43. The computer readable medium of claim 29 wherein the noise forces used in the step of combining thermal noise forces with the interatomic non-bonding forces are described by a gaussian distribution.

44. The computer readable medium of claim 29 wherein the instructions for the step of projecting out of said interatomic non-bonding forces and noise forces require that this step be accomplished by means of a matrix inversion of a set of simultaneous equations.

* * * * *